United States Patent
Osborn et al.

(10) Patent No.: US 12,404,553 B2
(45) Date of Patent: Sep. 2, 2025

(54) BIOMARKERS FOR BIPOLAR DISORDER AND SCHIZOPHRENIA

(71) Applicants: THE REGENTS OF THE UNIVERSITY OF CALIFORNIA, Oakland, CA (US); LAGUNA DIAGNOSTICS, LLC, The Villages, FL (US)

(72) Inventors: Terry W. Osborn, The Villages, FL (US); Marquis Vawter, Laguna Niguel, CA (US)

(73) Assignees: THE REGENTS OF THE UNIVERSITY OF CALIFORNIA, Oakland, CA (US); LAGUNA DIAGNOSTICS, LLC, The Villages, FL (US)

( * ) Notice: Subject to any disclaimer, the term of this patent is extended or adjusted under 35 U.S.C. 154(b) by 0 days.

(21) Appl. No.: 18/333,231

(22) Filed: Jun. 12, 2023

(65) Prior Publication Data

US 2023/0383354 A1   Nov. 30, 2023

Related U.S. Application Data

(63) Continuation of application No. 16/333,626, filed as application No. PCT/US2017/051716 on Sep. 15, 2017, now Pat. No. 11,713,486.

(60) Provisional application No. 62/395,159, filed on Sep. 15, 2016.

(51) Int. Cl.
*C12Q 1/6883* (2018.01)
*G01N 33/68* (2006.01)

(52) U.S. Cl.
CPC ....... *C12Q 1/6883* (2013.01); *G01N 33/6896* (2013.01); *C12Q 2600/158* (2013.01); *G01N 2800/302* (2013.01); *G01N 2800/304* (2013.01); *G01N 2800/60* (2013.01)

(58) Field of Classification Search
CPC ............ C12Q 1/6883; C12Q 2600/158; G01N 33/6896; G01N 2800/302; G01N 2800/304; G01N 2800/60; G01N 33/50
See application file for complete search history.

(56) References Cited

U.S. PATENT DOCUMENTS

| | | |
|---|---|---|
| 5,143,854 A | 9/1992 | Pirrung et al. |
| 5,384,261 A | 1/1995 | Winkler et al. |
| 5,424,186 A | 6/1995 | Fodor et al. |
| 5,445,934 A | 8/1995 | Fodor et al. |
| 5,677,195 A | 10/1997 | Winkler et al. |
| 5,708,153 A | 1/1998 | Dower et al. |
| 5,744,305 A | 4/1998 | Fodor et al. |
| 5,770,358 A | 6/1998 | Dower et al. |
| 5,789,162 A | 8/1998 | Dower et al. |
| 5,800,992 A | 9/1998 | Fodor et al. |
| 5,856,174 A | 1/1999 | Lipshutz et al. |
| 5,922,591 A | 7/1999 | Anderson et al. |
| 6,040,193 A | 3/2000 | Winkler et al. |
| 2008/0199866 A1 | 8/2008 | Akil et al. |
| 2014/0141986 A1 | 5/2014 | Spetzler et al. |

OTHER PUBLICATIONS

Mamdani, F., et al. 2015. Variable telomere length across post-mortem human brain regions and specific reduction in the hippocampus of major depressive disorder, Transl Psychiatry, 5: e636.
Martin, M. V., et al. 2009. Exon expression in lymphoblastoid cell lines from subjects with schizophrenia before and after glucose deprivation, BMC Med Genomics, 2: 62.
Middleton, F. A., et al. 2005. Gene expression analysis of peripheral blood leukocytes from discordant sib-pairs with schizophrenia and bipolar disorder reveals points of convergence between genetic and functional genomic approaches, Am J Med Genet B Neuropsychiatr Genet, 136B: 12-25.
Morgan, L. Z., et al. 2016. Quantitative Trait Locus and Brain Expression of HLA-DPA1 Offers Evidence of Shared Immune Alterations in Psychiatric Disorders, Microarrays (Basel), 5.
Munkholm, K., et al. 2014. Reduced mRNA expression of PTGDS in peripheral blood mononuclear cells of rapid-cycling bipolar disorder patients compared with healthy control subjects, Int J Neuropsychopharmacol, 18.
Naydenov, A. V., et al. 2007. Differences in lymphocyte electron transport gene expression levels between subjects with bipolar disorder and normal controls in response to glucose deprivation stress, Arch Gen Psychiatry, 64: 555-64.
Nishimura, Y., et al. 2007. Genome-wide expression profiling of lymphoblastoid cell lines distinguishes different forms of autism and reveals shared pathways, Hum Mol Genet, 16: 1682-98.
Perl, O., et al. 2006. Low levels of alpha7-nicotinic acetylcholine receptor mRNA on peripheral blood lymphocytes in schizophrenia and its association with illness severity, Neuropsychobiology, 53: 88-93.
Philibert, R. A., et al. 2007. Transcriptional profiling of lymphoblast lines from subjects with panic disorder, Am J Med Genet B Neuropsychiatr Genet, 144B: 674-82.
Philibert, R. A., et al. 2007. Transcriptional profiling of subjects from the Iowa adoption studies, Am J Med Genet B Neuropsychiatr Genet, 144B: 683-90.
Pradervand, S., et al. 2008. Affymetrix Whole-Transcript Human Gene 1.0 ST array is highly concordant with standard 3' expression arrays, Biotechniques, 44: 759-62.
Ramos, E. I., et al. 2014. Genetic variation in MKL2 and decreased downstream PCTAIRE1 expression in extreme, fatal primary human microcephaly, Clin Genet, 85: 423-32.
Richard, H., et al. 2010. Prediction of alternative isoforms from exon expression levels in RNA-Seq experiments, Nucleic Acids Res, 38: e112.

(Continued)

*Primary Examiner* — Sarae L Bausch
(74) *Attorney, Agent, or Firm* — ARRIGO, LEE, GUTTMAN & MOUTA-BELLUM, LLP; Carla Mouta-Bellum

(57) ABSTRACT

The present invention provides combinations of biomarkers that can be used in the diagnosis and differentiation of bipolar disorder and schizophrenia. The present invention therefore provides methods of differentiating, diagnosing and treating bipolar disorder and schizophrenia, by examining relevant proteins and RNA in a patient sample.

14 Claims, 12 Drawing Sheets

(56) References Cited

OTHER PUBLICATIONS

Rollins, B., et al. 2010. Analysis of whole genome biomarker expression in blood and brain, Am J Med Genet B Neuropsychiatr Genet, 153B: 919-36.
Ruderfer, D. M., et al. 2014. Polygenic dissection of diagnosis and clinical dimensions of bipolar disorder and schizophrenia, Mol Psychiatry, 19: 1017-24.
Sanders, A. R., et al. 2013. Transcriptome study of differential expression in schizophrenia, Hum Mol Genet, 22: 5001-14.
Scarr, E., et al. 2015. Biomarkers for Psychiatry: The Journey from Fantasy to Fact, a Report of the 2013 CINP Think Tank, Int J Neuropsychopharmacol, 18: pyv042.
Schizophrenia Working Group of the Psychiatric Genomics, Consortium. 2014. Biological insights from 108 schizophrenia-associated genetic loci, Nature, 511: 421-7.
Schoenbaum, M., et al. 2017. Twelve-Month Health Care Use and Mortality in Commercially Insured Young People With Incident Psychosis in the United States, Schizophr Bull, 43: 1262-72.
Segman, R. H., et al. 2005. Peripheral blood mononuclear cell gene expression profiles identify emergent post-traumatic stress disorder among trauma survivors, Mol Psychiatry, 10: 500-13, 425.
Sekar, A., et al. 2016. Schizophrenia risk from complex variation of complement component 4, Nature, 530: 177-83.
Sequeira, A., et al. 2008. Coding SNPs included in exon arrays for the study of psychiatric disorders, Mol Psychiatry, 13: 363-5.
Shen, S., et al. 2010. MADS+: discovery of differential splicing events from Affymetrix exon junction array data, Bioinformatics, 26: 268-9.
Tang, Y., et al. 2005. Blood gene expression profiling of neurologic diseases: a pilot microarray study, Arch Neurol, 62: 210-5.
Tomasik, J., et al. 2012. Blood test for schizophrenia, Eur Arch Psychiatry Clin Neurosci, 262 Suppl 2: S79-83.
Vawter, M. P., et al. 2007. Dysregulation of X-linked gene expression in Klinefelter's syndrome and association with verbal cognition, Am J Med Genet B Neuropsychiatr Genet, 144B: 728-34.
Vawter, M. P., et al. 2011. An integrative functional genomics approach for discovering biomarkers in schizophrenia, Brief Funct Genomics, 10: 387-99.
Weber, M. D., et al. 2017. Repeated Social Defeat, Neuroinflammation, and Behavior: Monocytes Carry the Signal, Neuropsychopharmacology, 42: 46-61.
Wu, J. Q., et al. 2016. Altered neural signaling and immune pathways in peripheral blood mononuclear cells of schizophrenia patients with cognitive impairment: A transcriptome analysis, Brain Behav Immun, 53: 194-206.
Xing, Y., et al. 2006. Probe selection and expression index computation of Affymetrix Exon Arrays, PLoS One, 1: e88.
Xing, Y., et al. 2007. Assessing the conservation of mammalian gene expression using high-density exon arrays, Mol Biol Evol, 24: 1283-5.
Xing, Y., et al. 2008. MADS: a new and improved method for analysis of differential alternative splicing by exon-tiling microarrays, RNA, 14: 1470-9.
Xu, W., et al. 2011. Human transcriptome array for high-throughput clinical studies, Proc Natl Acad Sci U S A, 108: 3707-12.
Xu, Y., et al. 2016. Altered expression of mRNA profiles in blood of early-onset schizophrenia, Sci Rep, 6: 16767.
Yao, Y., et al. 2008. Verification of proposed peripheral biomarkers in mononuclear cells of individuals with schizophrenia, J Psychiatr Res, 42: 639-43.
Vawter, M.P et al., Exon Array Biomarkers for the Differential Diagnosis of Schizophrenia and Bipolar Disorder, Molecular Neuropsychiatry 2017; 3:197-213, Apr. 10, 2018.
Cohen, O.S. et al., Transcriptomic Analysis of Postmortem Brain identifies Dysregulated Splicing Events in Novel Candidate Genes for Schizophrenia, National Institutes of Health, Schizophr Res. Dec. 2012; 142(1-3); 188-199, 30 pages.
Citrome, L., "A systematic review of meta-analyses of the efficacy of oral atypical antipsychotics for the treatment of adult patients with schizophrenia", Expert Opinion on Pharmacotherapy, vol. 13, Issue 11, Aug. 2012, 1545-7153.
Ogawa et al., "Mood Stabilizers and Antipsychotics for Acute Mania: A Systematic Review and Meta-Analysis of Combination/Augmentation Therapy Versus Monotherapy", International Journal of Neuropsychopharmacology, vol. 25, Issue 10, Oct. 2022, 839-852.
Enard et al. (Science. Apr. 12, 2002.; 296(5566):340-43).
Zhang (European Archives of Psychiatry and Clinical Neuroscience, 2002, 272:591-602).
Cheung (Cold Spring Harbor Symposia on Quant Bio., 2003, vol. LXVIII, pp. 403-407).
Cohen et al. Schizophrenia Research, 2012, vol. 142: 188-199.
Agarwal, A., et al. 2010. Comparison and calibration of transcriptome data from RNA-Seq and tiling arrays, BMC Genomics, 11: 383.
Anand, A., et al. 2016. Effects of Lithium Monotherapy for Bipolar Disorder on Gene Expression in Peripheral Lymphocytes, Mol Neuropsychiatry, 2: 115-23.
Begemann, M., et al. 2008. Episode-specific differential gene expression of peripheral blood mononuclear cells in rapid cycling supports novel treatment approaches, Mol Med, 14: 546-52.
Bemmo, A., et al. 2008. Gene expression and isoform variation analysis using Affymetrix Exon Arrays, BMC Genomics, 9: 529.
Benovoy, D., et al. 2008. Effect of polymorphisms within probe-target sequences on olignonucleotide microarray experiments, Nucleic Acids Res, 36: 4417-23.
Bomprezzi, R., et al. 2003. Gene expression profile in multiple sclerosis patients and healthy controls: identifying pathways relevant to disease, Hum Mol Genet, 12: 2191-9.
Borovecki, F., et al. 2005. Genome-wide expression profiling of human blood reveals biomarkers for Huntington's disease, Proc Natl Acad Sci U S A, 102: 11023-8.
Bowden, N. A., et al. 2006. Preliminary investigation of gene expression profiles in peripheral blood lymphocytes in schizophrenia, Schizophr Res, 82: 175-83.
Bradford, J. R., et al. 2010. A comparison of massively parallel nucleotide sequencing with oligonucleotide microarrays for global transcription profiling, BMC Genomics, 11: 282.
Brea, D., et al. 2009. Inflammatory and neuroimmunomodulatory changes in acute cerebral ischemia, Cerebrovasc Dis, 27 Suppl 1: 48-64.
Chan, M. K., et al. 2014. Applications of blood-based protein biomarker strategies in the study of psychiatric disorders, Prog Neurobiol, 122: 45-72.
Chan, M. K., et al. 2015. Development of a blood-based molecular biomarker test for identification of schizophrenia before disease onset, Transl Psychiatry, 5: e601.
Cloutier, M., et al. 2016. The Economic Burden of Schizophrenia in the United States in 2013, J Clin Psychiatry, 77: 764-71.
Cole, S. W., et al. 2007. Social regulation of gene expression in human leukocytes, Genome Biol, 8: R189.
De Jong, S., et al. 2012. A gene co-expression network in whole blood of schizophrenia patients is independent of antipsychotic-use and enriched for brain-expressed genes, PLoS One, 7: e39498.
Dilsaver, S. C. 2011. An estimate of the minimum economic burden of bipolar I and II disorders in the United States: 2009, J Affect Disord, 129: 79-83.
Downes, C. E., et al. 2010. Neural injury following stroke: are Toll-like receptors the link between the immune system and the CNS?, Br J Pharmacol, 160: 1872-88.
Duan, S., et al. 2008. Genetic architecture of transcript-level variation in humans, Am J Hum Genet, 82: 1101-13.
Duan, S., et al. 2009. Expression and alternative splicing of folate pathway genes in HapMap lymphoblastoid cell lines, Pharmacogenomics, 10: 549-63.
Duan, S., et al. 2008. SNPinProbe_1.0: a database for filtering out probes in the Affymetrix GeneChip human exon 1.0 ST array potentially affected by SNPs, Bioinformation, 2: 469-70.
Evans, S. J., et al. 2012. Fats and factors: lipid profiles associate with personality factors and suicidal history in bipolar subjects, PLoS One, 7: e29297.
Fodor, S. P., et al. 1991. Light-directed, spatially addressable parallel chemical synthesis, Science, 251: 767-73.

(56) References Cited

OTHER PUBLICATIONS

Fraser, H. B., et al. 2009. Common polymorphic transcript variation in human disease, Genome Res, 19: 567-75.

Fromer, M., et al. 2016. Gene expression elucidates functional impact of polygenic risk for schizophrenia, Nat Neurosci, 19: 1442-53.

Gamazon, E. R., et al. 2010. Comprehensive survey of SNPs in the Affymetrix exon array using the 1000 Genomes dataset, PLoS One, 5: e9366.

Gamazon, E. R., et al. 2010. SCAN: SNP and copy number annotation, Bioinformatics, 26: 259-62.

Gelderblom, M., et al. 2009. Temporal and spatial dynamics of cerebral immune cell accumulation in stroke, Stroke, 40: 1849-57.

Giannone, S., et al. 2004. Gene expression profile analysis in human T lymphocytes from patients with Down Syndrome, Ann Hum Genet, 68: 546-54.

Glatt, S. J., et al. 2009. Alternatively Spliced Genes as Biomarkers for Schizophrenia, Bipolar Disorder and Psychosis: A Blood-Based Spliceome-Profiling Exploratory Study, Curr Pharmacogenomics Person Med, 7: 164-88.

Glatt, S. J., et al. 2005. Comparative gene expression analysis of blood and brain provides concurrent validation of SELENBP1 up-regulation in schizophrenia, Proc Natl Acad Sci U S A, 102: 15533-8.

Glatt, S. J., et al. 2011. Similarities and differences in peripheral blood gene-expression signatures of individuals with schizophrenia and their first-degree biological relatives, Am J Med Genet B Neuropsychiatr Genet, 156B: 869-87.

Haenisch, F., et al. 2016. Towards a blood-based diagnostic panel for bipolar disorder, Brain Behav Immun, 52: 49-57.

Hawrylycz, M. J., et al. 2012. An anatomically comprehensive atlas of the adult human brain transcriptome, Nature, 489: 391-99.

Heinzen, E. L., et al. 2008. Tissue-specific genetic control of splicing: implications for the study of complex traits, PLoS Biol, 6: e1.

Hess, J. L., et al. 2016. Transcriptome-wide mega-analyses reveal joint dysregulation of immunologic genes and transcription regulators in brain and blood in schizophrenia, Schizophr Res, 176: 114-24.

Horvath, S., et al. 2014. Immune system disturbances in schizophrenia, Biol Psychiatry, 75: 316-23.

Hou, L., et al. 2016. Genome-wide association study of 40,000 individuals identifies two novel loci associated with bipolar disorder, Hum Mol Genet, 25: 3383-94.

International Schizophrenia, Consortium, et al. 2009. Common polygenic variation contributes to risk of schizophrenia and bipolar disorder, Nature, 460: 748-52.

Kapur, K., et al. 2008. Cross-hybridization modeling on Affymetrix exon arrays, Bioinformatics, 24: 2887-93.

Kapur, K., et al. 2007. Exon arrays provide accurate assessments of gene expression, Genome Biol, 8: R82.

Kumarasinghe, N., et al. 2013. Gene expression profiling in treatment-naive schizophrenia patients identifies abnormalities in biological pathways involving AKT1 that are corrected by antipsychotic medication, Int J Neuropsychopharmacol, 16: 1483-503.

Kwan, T., et al. 2008. Genome-wide analysis of transcript isoform variation in humans, Nat Genet, 40: 225-31.

Le-Niculescu, H., et al. 2011. Convergent functional genomics of anxiety disorders: translational identification of genes, biomarkers, pathways and mechanisms, Transl Psychiatry, 1: e9.

Liew, C. C., et al. 2006. The peripheral blood transcriptome dynamically reflects system wide biology: a potential diagnostic tool, J Lab Clin Med, 147: 126-32.

Lin, L., et al. 2009. Using high-density exon arrays to profile gene expression in closely related species, Nucleic Acids Res, 37: e90.

Liu, S., et al. 2011. A comparison of RNA-Seq and high-density exon array for detecting differential gene expression between closely related species, Nucleic Acids Res, 39: 578-88.

Liu, Y., et al. 2009. Elevated delta-6 desaturase (FADS2) expression in the postmortem prefrontal cortex of schizophrenic patients: relationship with fatty acid composition, Schizophr Res, 109: 113-20.

Liu, Y., et al. 2011. Elevated Delta-6 desaturase (FADS2) gene expression in the prefrontal cortex of patients with bipolar disorder, J Psychiatr Res, 45: 269-72.

Maes, O. C., et al. 2007. Transcriptional profiling of Alzheimer blood mononuclear cells by microarray, Neurobiol Aging, 28: 1795-809.

Mamdani, F., et al. 2013. Coding and noncoding gene expression biomarkers in mood disorders and schizophrenia, Dis Markers, 35: 11-21.

Geddes et al. 2013, Comparative efficacy and tolerability of 15 antipsychotic drugs in schizophrenia: a multiple-treatments meta-analysis, Lancet 2013; 382: 951-62.

Perlis et al. 2006, Atypical Antipsychotics in the treatment of mania: a meta-analysis of randomized, placebo-controlled trials, J Clin Psychiatry 2006; 67:509-516, 509.

BIOMARKERS FOR BIPOLAR DISORDER AND SCHIZOPHRENIA

CROSS-REFERENCE TO RELATED APPLICATIONS

This application claims the benefit of U.S. application Ser. No. 16/333,626, filed Mar. 15, 2019, which is a U.S. national phase application filed under 35 U.S.C. § 371 claiming priority to International Patent Application No. PCT/US17/51716, filed Sep. 15, 2017, which claims priority to U.S. Provisional Application No. 63/395,159, filed Sep. 15, 2016, the contents of each of which are incorporated by reference herein in their entireties.

STATEMENT REGARDING FEDERALLY SPONSORED RESEARCH OR DEVELOPMENT

This invention was made with government support under R43MH090806 awarded by the National Institutes of Health (NIH). The government has certain rights in the invention.

BACKGROUND OF THE INVENTION

Schizophrenia and bipolar disorder are chronic, severe and disabling brain disorders that affect about 1 and 2 percent of age 18 and older U.S. population, respectively. Despite moderately effective treatments, such as antipsychotic medications and psychosocial interventions, people with schizophrenia (SZ) and bipolar disorder (BD) often do not receive timely treatment because of misdiagnosis until the disease is already well-established with recurrent episodes of psychosis and mood dysregulation. These episodes result in costly multiple hospitalizations and disabilities that can last for decades. Ideally, successful diagnostic tests could address the significant clinical problem of early identification and enable more timely initiation of treatments.

Over 2,000,000 individuals are clinically diagnosed as suffering with schizophrenia (SZ) in the U.S. Over 100,000 adolescent Americans suffer from an initial episode of psychosis each year. Currently, no 'objective' clinical laboratory test exists to accurately diagnose their disease, and there are no FDA approved biomarkers for psychotic disorders such as SZ or mood disorders associated with psychosis such as bipolar disorder (BD). Physicians cannot use brain biopsies of living patients for diagnosis of neuropsychiatric disorders. Instead, physicians rely upon clinical observation and the patient's history of reported symptoms. Consequently, if physicians misdiagnose similarly presenting diseases like SZ and BD, there can be a lag in treatment and increase in the suicide rate. Following an initial episode of psychosis among individuals aged 16-30, there is a 24-fold increase in the risk of death in the following year (Schoenbaum, Twelve-Month Health Care Use and Mortality in Commercially Insured Young People With Incident Psychosis in the United States. Schizophrenia Bulletin 2017). This study points towards a lack of treatment (61% did not receive any antipsychotic medication) after initial presentation with psychosis and even higher rates in those dying within 12 months of an initial episode of psychosis (Schoenbaum, Twelve-Month Health Care Use and Mortality in Commercially Insured Young People With Incident Psychosis in the United States. Schizophrenia Bulletin 2017). Through clinical observations, these diseases take months or even years to diagnose definitively and to appropriately prescribe disease-matched medications for effective treatment. The mental health field could benefit greatly from commercial blood-based biomarker tests that discriminate between patients without a psychiatric disorder and those with SZ or BD.

A growing body of work has demonstrated the potential utility of RNA diagnostic tools with peripheral samples such as whole blood, peripheral blood mononuclear cells, and lymphoblastic cell lines in multiple studies of SZ and BD (Begemann et al., Mol Med 2008; 14(9-10): 546-552; Bowden et al., Schizophr Res 2006; 82(2-3): 175-183; de Jong S et al., PLoS One 2012; 7(6): e39498; Glatt et al., Proc Natl Acad Sci USA 2005; 102(43): 15533-15538; Middleton et al., Am J Med Genet B Neuropsychiatr Genet 2005; 136B(1): 12-25; Naydenov et al., Arch Gen Psychiatry 2007; 64(5): 555-564; Merl et al., Neuropsychobiology 2006; 53(2): 88-93; Sanders et al., Hum Mol Genet 2013; 22(24): 5001-5014; Yao et al., J Psychiatr Res 2008; 42(8): 639-643). There have also been large studies that have used whole genome RNA expression to compare healthy controls and disorders such as Alzheimer's disease (Maes et al., Neurobiol Aging 2007; 28(12): 1795-1809), autism (Nishimura et al., Hum Mol Genet 2007; 16(14): 1682-1698), Down's Syndrome (Giannone et al., Ann Hum Genet 2004; 68(Pt 6): 546-554), epilepsy (Tang et al., Arch Neurol 2005; 62(2): 210-215), Tourette's Syndrome (Tang et al., Arch Neurol 2005; 62(2): 210-215), Huntington's Disease (Borovecki et al., Proc Natl Acad Sci USA 2005; 102(31): 11023-11028), Klinefelter's Syndrome (KS) (Vawter et al., Am J Med Genet B Neuropsychiatr Genet 2007; 144B(6): 728-734), multiple sclerosis (Bomprezzi et al., Hum Mol Genet 2003; 12(17): 2191-2199), smoking and major depression (Philibert et al., Am J Med Genet B Neuropsychiatr Genet 2007; 144B(5): 683-690), panic disorder (Philibert et al., Am J Med Genet B Neuropsychiatr Genet 2007; 144B(5): 674-682), post-traumatic stress disorder (Segman et al., Mol Psychiatry 2005; 10(5): 500-513, 425), and subjective social isolation (loneliness) (Cole et at, Genome Biol 2007; 8(9): R189).

A tremendous effort has been expended into GWAS of schizophrenia (Consortium. Nature 2014; 511(7510): 421-427) and bipolar disorder (Hou et al., Hum Mol Genet 2016; 25(15): 3383-3394), however, there is a lack of consensus regarding the specific genes that cause schizophrenia or bipolar disorder; with shared genetic factors across these disorders (Iftuderfer et al., Mol Psychiatry 2014; 19(9): 1017-1024). More importantly, which combinations of interacting genes that actually cause each illness as opposed to polygenic susceptibilities for psychiatric endophenotypes are unknown. Estimates of several hundred genes of small effect size were published from the largest international genetic study of SZ (Purcell et al., Nature 2009; 460(7256): 748-752) to the possibility that thousands of genes are involved in the pathogenesis of schizophrenia (Profiler et al., Nat Neurosci 2016; 19(11): 1442-1453). Dysregulation of friRNA could potentially help to define sets of genes relevant to pathophysiology, treatment, or secondary to these causes.

Thus, there is an urgent need in the art for compositions and methods for objectively diagnosing SZ and BD, to reduce duration of untreated psychosis by earlier detection to help establish rapid and informative patient decisions. The present invention addresses these needs.

SUMMARY

In one embodiment, the invention relates to a method of diagnosing schizophrenia (SZ) or bipolar disorder (BD) in a subject, the method comprising: a) determining the expression level of at least two biomarker genes selected from the group consisting of SH3Y1,1, TBC1D1, TCEA3, SLC44A5, HADHA, CPA3, IL5RA, OXTR, CCDC109B, TREML4, TRIM4, PTGDS, GYLTL1B, FADS2, CRIP2, HPR, DDX5, EEF2, ZMYND8 and HLA-DRB5 in a sample of the subject, b) determining the probability of the sample being from a subject with or without SZ or BD, and c) diagnosing the subject as having SZ or BD on the basis of the determined result from the sample as compared to a pre-determined cut-off.

In one embodiment, the method comprises evaluating the expression levels of at least two of TCEA3, SLC44A5, IL5RA, GYLTL1 B and DDX5, determining the probability of the sample being from a subject with schizophrenia, and diagnosing the subject with SZ when the probability of the sample being from a subject with schizophrenia is greater than 0.499.

In one embodiment, the method comprises evaluating the expression levels of at least two of HPR, TREML4, PTGDS, CPA3, TRIM4 and SLC44A5, determining the probability of the sample being from a subject with schizophrenia, and diagnosing the subject with SZ when the probability of the sample being from a subject with schizophrenia is greater than 0.549.

In one embodiment, the method comprises evaluating the expression levels of at least two of SLC44A5, CPA3, TREML4, TRIM4, PTGDS and SH3YL1, determining the probability of the sample being from a subject with schizophrenia, and diagnosing the subject with SZ when the probability of the sample being from a subject with schizophrenia is greater than or equal to 0.411.

In one embodiment, the method comprises evaluating the expression levels of at least two of PTGDS, HLA-DRB5, OXTR and FADS2, determining the probability of the sample being from a healthy subject, and diagnosing the subject with BD when the probability of the sample being from a healthy subject is less than or equal to 0.659.

In one embodiment, the method comprises evaluating the expression levels of at least two of CRIP2, CPA3, OXTR, TRIM4, PTGDS and SH3YL1, determining the probability of the sample being from a subject with BD, and diagnosing the subject with BD when the probability of the sample being from a subject with BD is greater than or equal to 0.452.

In one embodiment, the method comprises evaluating the expression levels of at least two of SLC44A5, HADHA, CPA3, OXTR, CCDC109B, TREML4, TRIM4, PTGDS, GYILTL1B, HPR and ZMYND8, determining the probability of the sample being from a healthy subject, and diagnosing the subject with SZ or BD when the probability of the sample being from a healthy subject is less than or equal to 0.1518. In one embodiment, the method further comprises evaluating the expression levels of at least two of CRIP2, OXTR and FADS2 in the sample from the subject, wherein the probability of the sample being from a healthy subject was determined as less than or equal to 0.1518, determining the probability of the sample being from a BD subject, diagnosing the subject with SZ when the probability of the sample being from a BD subject is less than or equal to 0.2857, and diagnosing the subject with RD when the probability of the sample being from a BD subject is greater than 0.2857. In one embodiment, the method further comprises evaluating the expression levels of at least two of TCEA3, SLC44A5, IL5RA, GYLTL1B and DDX5 in the sample from the subject, wherein the probability of the sample being from a healthy subject was determined as greater than 0.1518, determining the probability of the sample being from a subject with schizophrenia, and diagnosing the subject with SZ when the probability of the sample being from a subject with schizophrenia is greater than 0.499. In one embodiment, the method further comprises evaluating the expression levels of at least two of PTGDS, HLA-DRB5, OXTR and FADS2 in the sample from the subject, wherein the probability of the sample being from a healthy subject was determined as greater than 0.1518, determining the probability of the sample being from a healthy subject, and diagnosing the subject with BD when the probability of the sample being from a healthy subject is less than or equal to 0.659.

In one embodiment, the method comprises evaluating the expression levels of at least two of SLC44A5, CPA3, CRIP2, TRIM4, PTGDS and SH3YL1, determining the probability of the sample being from a subject having SZ or RD, and diagnosing the subject with SZ or BD when the probability of the sample being from a subject having SZ or BD is greater than or equal to 0.466. In one embodiment, the method further comprises evaluating the expression levels of at least two of SH3YL1, OXTR, PTGDS, CPA3, TBC1D1, and TCEA3, determining the probability of the sample being from a subject with SZ, diagnosing the subject with SZ when the probability of the sample being from a subject with SZ is greater than or equal to 0.584, and diagnosing the subject with BD when the probability of the sample being from a subject with SZ is less than 0.584.

In one embodiment, the method comprises evaluating the expression levels of at least two of TCEA3, SLC44A5, IL5RA, GYLTL1B and DDX5, determining the probability of the sample being from a healthy subject, and diagnosing the subject with SZ when the probability of the sample being from a healthy subject is less than or equal to 0.3323. In one embodiment, the expression level of at least two biomarker genes is determined from data generated from the Nanostring platform.

In one embodiment, the method further comprises treating the subject for the diagnosed SZ or BD.

In one embodiment, the expression level of at least two biomarker genes is determined from data generated from a platform selected from Affymetrix exon array and Nanostring.

In one embodiment, the invention relates to a method of identifying a subject as belonging to the normal population with respect to BD or SZ, the method comprising: a) determining the expression level of at least two biomarker genes selected from the group consisting of SH3YL1, TBC1D1, TCEA3, SLC44A5, HADHA, CPA3, IL5RA, OXTR, CCDC109B, TREML4, TRIM4, PTGDS, GYLTL1B, FADS2, CRIP2, HPR, DDX5, EEF2, ZMYND8 and HLA-DRB5 in a sample of the subject, b) determining the probability of the sample being from a subject with or without SZ or BD, and c) identifying the subject as belonging to the normal population on the basis of the determined result from the sample as compared to a pre-determined cut-off.

In one embodiment, the method comprises evaluating the expression levels of at least two of SLC44A5, HADHA, CPA3, OXTR, CCDC109B, TREML4, TRIM4, PTGDS, GYLTL1B, HPR and ZMYND8, determining the probability of the sample being from a healthy subject, and identifying the subject as being from the normal population with respect to BD and SZ when the probability of the sample being from a healthy subject is greater than 0.1518. In one embodiment, the method further comprises evaluating the expression levels of at least two of TCEA3, SLC44A5, IL5RA, GYLTL1B and DDX5 in the sample from the subject, wherein the probability of the sample being from a healthy subject was determined as greater than 0.1518, determining the probability of the sample being from a subject with schizophrenia, and identifying the subject as being from the normal population with regard to SZ when the probability of the sample being from a subject with schizophrenia is less than or equal to 0.499. In one embodiment, the method further comprises evaluating the expression levels of at least two of PTGDS, HLA-DRB5, OXTR and FADS2 in the sample from the subject, wherein the probability of the sample being from a healthy subject was determined as greater than 0.1518, determining the probability of the sample being from a healthy subject, and identifying the subject as being from the normal population with regard to BD when the probability of the sample being from a healthy subject is greater than 0.659.

In one embodiment, the expression level of at least two biomarker genes is determined from data generated from a platform selected from Affymetrix exon array and Nanostring.

In one embodiment, the method comprises evaluating the expression levels of at least two of TCEA3, SLC44A5, IL5RA, GYLTL1B and DDX5, determining the probability of the sample being from a healthy subject, and identifying the subject as being from the normal population with respect to SZ when the probability of the sample being from a healthy subject is greater than 0.3323. In one embodiment, the expression level of at least two biomarker genes is determined from data generated from the Nanostring platform.

In one embodiment, the invention relates to a method of differentially diagnosing a subject in need thereof as having a disorder selected from the group consisting of SZ and BD, the method comprising: a) determining the expression level of at least two biomarker genes selected from the group consisting of SH3YL1, TBC1D1, TCEA3, SLC44A5, HADHA, CPA3, IL5RA, OXTR, CCDC109B, TREML4, TRIM4, PTGDS, GYLTL1B, FADS2, CRIP2, HPR, DDX5, EEF2, ZMYND8 and HLA-DRB5 in a sample of the subject; b) determining the probability of the sample being from a subject having a disorder selected from the group consisting of SZ and BD; and c) differentially diagnosing the subject as having a disorder selected from the group consisting of SZ and BD on the basis of the determined result from the sample as compared to a pre-determined cut-off.

In one embodiment, the method comprises evaluating the expression levels of at least two of CRTP2, OXTR and FADS2 in the sample from the subject, determining the probability of the sample being from a BD subject, diagnosing the subject with SZ when the probability of the sample being from a BD subject is less than or equal to 0.2857, and diagnosing the subject with BD when the probability of the sample being from a BD subject is greater than 0.2857.

In one embodiment, the subject has a prior diagnosis of a disorder selected from the group consisting of SZ and BD.

In one embodiment, the method further comprises treating the subject for the diagnosed SZ or BD.

In one embodiment, the expression level of at least two biomarker genes is determined from data generated from a platform selected from Affymetrix exon array and Nanostring.

BRIEF DESCRIPTION OF THE DRAWINGS

The following detailed description of embodiments of the invention will be better understood when read in conjunction with the appended drawings. For the purpose of illustrating the invention, drawings are included. It should be understood, however, that the invention is not limited to the precise arrangements and instrumentalities of the embodiments shown in the drawings.

DETAILED DESCRIPTION

Figure 1:
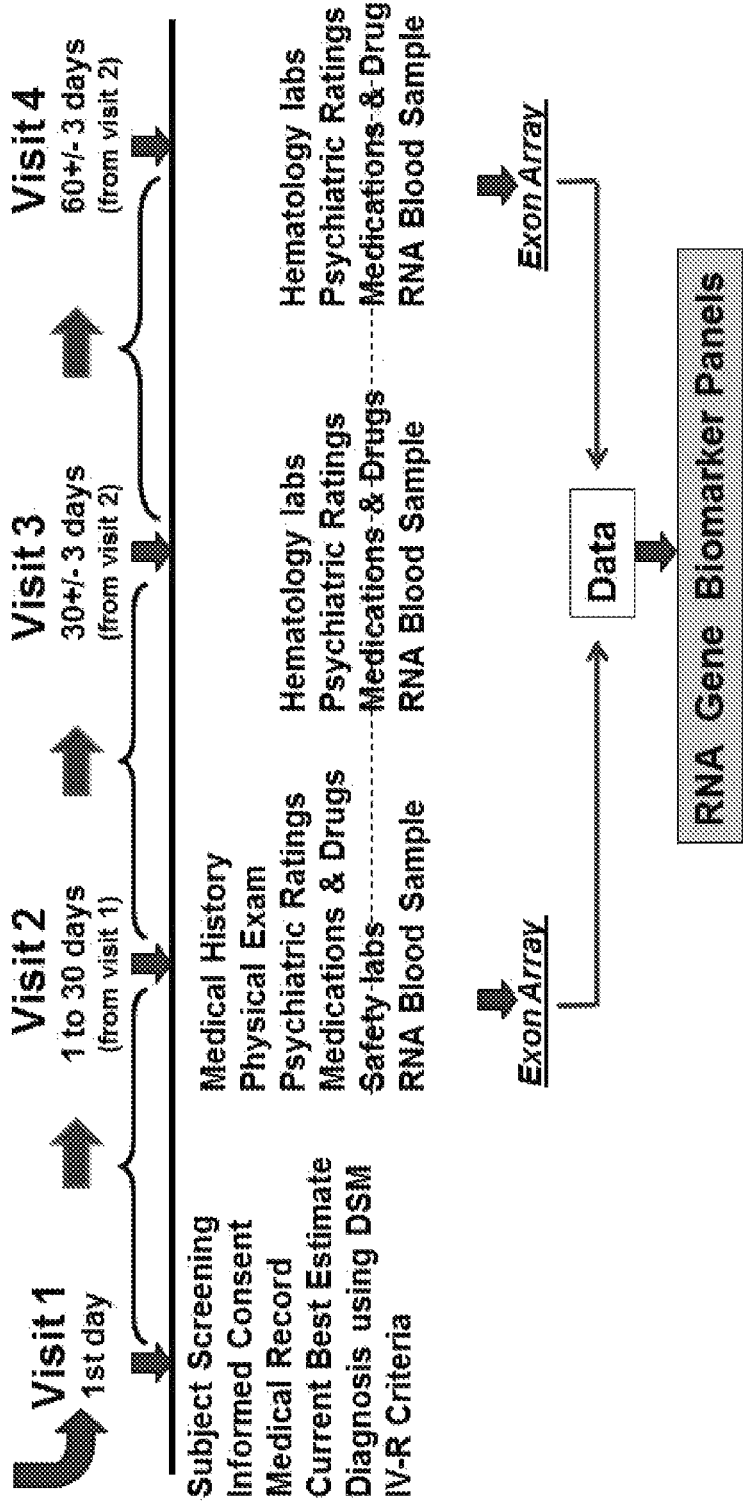
FIG. 1 depicts a schematic of a clinical study design to evaluate potential RNA gene biomarkers.

The present invention provides biomarkers that can discriminate between normal, BD and SZ subjects. The biomarkers of the invention can be used to screen, assess risk, diagnose and monitor the onset or progression of psychotic disorders and mood disorders. The biomarkers of the invention can be used to identify subjects in need of treatment for BD and SZ.

The present invention therefore provides compositions and methods of diagnosing a subject as having SZ or BD, by examining relevant biomarkers and their expression. In one embodiment, biomarker expression includes transcription into messenger RNA (mRNA) and/or translation into protein, as well as transcription into types of RNA such as transfer RNA (tRNA) and ribosomal RNA (rRNA) that are not translated into protein.

In one embodiment, the invention provides a method for diagnosing a subject with SZ or BD. In one embodiment, the assay includes detecting expression of relevant biomarkers. In one embodiment, the method includes detecting expression of a combination of biomarker genes. In one embodiment, the combination of biomarker genes is at least two genes selected from the group SH3YL1, TBC1D1, TCEA3, SLC44A5, HADHA, CPA3, IL5RA, OXTR, CCDC109B, TREML4, TRIM4, PTGDS, GYLTL1B, FADS2, CRIP2, HPR, DDX5, EEF2, ZMYND8 and HLA-DRB5. In one embodiment, the combination of genes is at least two genes selected from the group TCEA3, SLC44A5, HADHA, CPA3, IL5RA, OXTR, CCDC109B, TREML4, TRIM4, PTGDS, GYLTL1B, FADS2, CRIP2, HPR, DDX5, EEF2, ZMYND8 and HLA-DRB5.

In one embodiment, the invention provides method for diagnosing a subject with SZ. In one embodiment, the method includes evaluating expression of one or more relevant biomarkers. In one embodiment, the method includes detecting expression of a combination of biomarker genes. In one embodiment, the combination of biomarker genes is at least two of TCEA3, SLC44A5, IL5RA, GYLTL1B and DDX5. In one embodiment, the combination of genes is at least two of HPR, TREML4, PTGDS, CPA3, TRIM4 and SLC44A5. In one embodiment, the combination of genes is at least two of SLC44A5, CPA3, TREML4, TRIM4, PTGDS and SH3YL1. In one embodiment, expression of the combination of genes is used to determine the probability of a patient having SZ. In one embodiment, a patient is diagnosed as having SZ on the basis of the probability of the condition as compared to a pre-determined cut-off from a logistical regression model for the specific set of genes analyzed.

In one embodiment, the invention provides a method for diagnosing a subject with BD. In one embodiment, the method includes evaluating expression of one or more relevant biomarkers as compared to a comparator control. In one embodiment, the method includes detecting expression of a combination of biomarker genes. In one embodiment, the combination of biomarker genes is at least two of PTGDS, HLA-DRB5, OXTR and FADS2. In one embodiment, the combination of biomarker genes is at least two of CRIP2, CPA3, OXTR, TRIM41, PTGDS and SH3YL1. In one embodiment, expression of the combination of biomarker genes is used to determine the probability of a patient having BD. In one embodiment, a patient is diagnosed as having BD on the basis of the probability of the condition as compared to a pre-determined cut-off from a logistical regression model for the specific set of genes analyzed.

In one embodiment, the invention provides a method for differentiating between a subject with SZ or BD and a healthy subject. In one embodiment, the method includes evaluating expression of one or more relevant biomarkers as compared to a comparator control. In one embodiment, the method includes detecting expression of a combination of biomarker genes. In one embodiment, the combination of biomarker genes is at least two of SLC44A5, HADHA, CPA3, OXTR, CCDC109B, TREML4, TRIM4, PTGDS, GYLTL1B, HPR and ZMYND8. In one embodiment, the combination of biomarker genes is at least two of SLC44A5, CPA3, CRIP2, TRLM4, PTGDS and SH3YL1. In one embodiment, a patient is diagnosed as having SZ or BD on the basis of the probability of having one of the conditions as compared to a pre-determined cut-off from a logistical regression model for the specific set of genes analyzed.

In one embodiment, the method further provides for differentially diagnosing a subject characterized as having "SZ or BD" as having "BD" or "SZ." In one embodiment, the method comprises evaluating expression of a combination of relevant biomarkers in a subject having been identified as having "SZ or BD". In one embodiment, the combination of biomarker genes is at least two of CRIP2, OXTR and FADS2. In one embodiment, the combination of biomarker genes is at least two of SH3Y11, OXTR, PTGDS, CPA3, TBC1D1, and TCEA3. In one embodiment, expression of the combination of biomarker genes is used to determine the probability of a patient having "BD" or "SZ". In one embodiment, a patient is diagnosed as having SZ or BD on the basis of the probability of each condition as compared to a pre-determined cut-off from a logistical regression model for the specific set of genes analyzed.

In one embodiment, the method is useful for differentiating between "SZ" and "BD" in a subject. In one embodiment, the subject has a prior diagnosis of "SZ" or "BD". In one embodiment, a subject has no prior diagnosis of either "SZ" or "BD".

In one embodiment, a prior diagnosis of either "SZ" or "BD" is confirmed using the methods of the invention. In one embodiment, a prior diagnosis of either "SZ" or "BD" is identified as being a misdiagnosis either "SZ" or "BD" based on the methods of the invention. Therefore, in one embodiment, the invention provides a method of correctly diagnosing a subject with a prior diagnosis of "SZ" as having "BD," In an alternative embodiment, the invention provides a method of correctly diagnosing a subject with a prior diagnosis of "BD" as having "SZ."

In one embodiment, the invention provides a multi-step method for differentiating or diagnosing a subject as having "SZ" or "BD." In one embodiment, the invention comprises a first step of distinguishing a subject having "SZ or BD" from the normal population. In one embodiment, the method comprises a further step of differentially diagnosing a subject identified as having as having "SZ or BD" as having either "SZ" or "BD." In one embodiment, the method comprises a further step of performing a secondary analysis for "SZ" on a subject identified as having as belonging to the normal population. In one embodiment, the method comprises a further step of performing a secondary analysis for "BD" on a subject identified as having as belonging to the normal population. In one embodiment, the method includes detecting expression of different combinations of relevant biomarkers for each determination. In one embodiment, the method further includes using logistic regression models to identify whether expression of a combination of biomarkers is above or below a predetermined cut-off.

In one exemplary embodiment, the method includes detecting expression of a first combination of genes to distinguishing a subject having "SZ or BD" from the normal population. In one embodiment, the first combination of genes is at least two of SLC44A5, HAMA, CPA3, OXTR, CCDC109B, TREML4, TRIM4, PTGDS, GYLTL1B, HPR and ZMYND8. In one embodiment, a result of a logistic regression model, based on the expression at a combination of genes, is determined, wherein the result is the probability of a sample being from a healthy subject. In one embodiment, if the probability of a sample being from a healthy subject is less than or equal to a pre-determined cut-off then the sample is identified as being from a subject having SZ or RD.

In one embodiment, a pre-determined cut-off is 0.1518.

In one embodiment, a subject identified as having "SZ or BD" is further evaluated at a second combination of genes to differentially diagnose the subject as having "SZ" or "BD." In one embodiment, the second combination of genes is at least two of CRIP2, OXTR and FADS2. In one embodiment, a result of a logistic regression model, based on the expression at a combination of genes, is determined, wherein the result is the probability of a sample being from a subject with BD. In one embodiment, if the probability of a sample being from a subject with BD is less than or equal to a pre-determined cut-off then the sample is identified as being from a subject having SZ. In one embodiment, if the probability of a sample being from a subject with BD is greater than a pre-determined cut-off then the sample is identified as being from a subject having BD. In one embodiment, a pre-determined cut-off is 0.2857.

In one embodiment, a subject identified as likely being from the normal population is further evaluated at one or more additional combination of genes useful for diagnosing the subject as having "SZ" or "BD." In one embodiment, an additional combination of genes useful for diagnosing "SZ" is at least two of TCEA3, SLC44A5, IL5RA, GYLTL1B and DDX5. In one embodiment, an additional combination of genes useful for diagnosing "BD" is at least two of PTGDS, HLA-DRB5, OXTR and FADS2. In one embodiment, a result of a logistic regression model, based on the expression at a combination of genes, is determined, wherein the result is the probability of a sample being from a subject with "BD" or "SZ." In one embodiment, if the probability of a sample being from a healthy subject is less than or equal to a pre-determined cut-off then the sample is identified as being from a subject having "BD" or "SZ." In one embodiment, if the probability of a sample being from a subject with "BD" or "SZ" is greater than a pre-determined cut-off then the sample is identified as being from a subject having "BD" or "SZ".

Accordingly, in some embodiments of the invention, methods for diagnosing SZ or BD in a subject is provided. The methods comprise a) providing a sample from the subject; b) analyzing the sample with an assay that specifically detects a combination of biomarkers of the invention in the sample; c) evaluating gene expression at one or more combination of biomarkers and d) diagnosing SZ or BD in the subject.

In one embodiment, the step of analyzing the sample with an assay that specifically detects a combination of biomarkers of the invention in the sample comprises contacting a sample from a subject with an assay for detecting the expression levels of at least two biomarkers selected from the group SH3YL1, TBC1D1, TCEA3, SLC44A5, HAMA, CPA3, IL5RA, OXTR, CCDC10913, TREM4, TRIM4, PTGDS, GYLTL1B, FADS2, CRIP2, HPR, DDXS, EEF2, ZMYND8 and HLA-DRB5 in the sample. In one embodiment, the assay detected the expression levels of at least two of the biomarkers selected from the group TCEA3, SLC44A5, HADHA, CPA3, IL5RA, OXTR, CCDC109B, TREML4, TRIM4, PTGDS, FADS2, CRIP2, HPR, DDX5, EEF2, ZMYND8 and HLA-DRB5. In one embodiment, the assay detects the expression levels of at least two of the biomarkers selected from the group TCEA3, SIX44A5, IL5RA, GYLTL1B and DDX5. In one embodiment, the assay detects the expression levels of at least two of the biomarkers selected from the group HPR, TREML4, PTGDS, CPA3, TRIM4 and SLC44A5. In one embodiment, the assay detects the expression levels of at least two of the biomarkers selected from the group SLC44A5, CPA3, TREML4, TRIM4, PTGDS and SH3YL1. In one embodiment, the assay detects the expression levels of at least two of the biomarkers selected from the group PTGDS, HLA-DRB5, OXTR and FADS2. In one embodiment, the assay detects the expression levels of at least two of the biomarkers selected from the group CR1P2, CPA3, OXTR, TRIM4, PTGDS and SH3YL1. In one embodiment, the assay detects the expression levels of at least two of the biomarkers selected from the group SLC44A5, HADHA, CPA3, OXTR, CCDC109B, TREML4, TRIM4, PTGDS, GYLTL1B, HPR and ZMYND8. In one embodiment, the assay detects the expression levels of at least two of the biomarkers selected from the group SLC44A5, CPA3, CRIP2, TRIM4, PTGDS and SH3Y1L1. In one embodiment, the assay detects the expression levels of at least two of the biomarkers selected from the group CRIP2, OXTR and FADS2. In one embodiment, the assay detects the expression levels of at least two of the biomarkers selected from the group SH3YL1, OXTR, PTGDS, CPA3, TBC1D1, and TCEA3.

In one embodiment, the step of evaluating gene expression of one or more combinations of biomarkers comprises comparing the expression levels of the combination of at least two biomarkers selected from the group SH3YL1, TBC1D1, TCEA3, SLC44A5, HADHA, CPA3, IL5RA, OXTR, CCDC109B, TREML4, TRIM4, PTGDS, GYLTL1B, FADS2, CRIP2, HPR, DDX5, EEF2, ZMYND8 and HLA-DRB5 between the sample and a comparator control. In one embodiment, the comparator control is expression levels in a normal subject, or a healthy profile. In one embodiment, the comparator control is a predetermined probability cut-off based on logistical regression analysis.

In one embodiment, expression of the full length protein is detected. In one embodiment, expression of a fragment of the full length protein is detected.

In one embodiment, the biomarker types comprise mRNA biomarkers. In various embodiments, the mRNA is detected by at least one of mass spectroscopy, PCR microarray, thermal sequencing, capillary array sequencing, solid phase sequencing, and the like.

In another embodiment, the biomarker types comprise polypeptide biomarkers. In various embodiments, the polypeptide is detected by at least one of ELISA, Western blot, flow cytometry, immunofluorescence, immunohistochemistry, mass spectroscopy, and the like.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±40% or ±20% or ±10%, ±5%, ±1%, or ±0.1% from the specified value, as such variations are appropriate.

The term "amplification" refers to the operation by which the number of copies of a target nucleotide sequence present in a sample is multiplied.

As used herein, the term "marker" or "biomarker" is meant to include a parameter (e.g., RNA, polypeptide, etc.) which is useful according to this invention for determining the presence and/or severity and/or stage of SZ or BD.

The term "control or reference standard or comparator" describes a material comprising none, or a normal, low, or high level of one of more of the marker (or biomarker) expression products of one or more the markers (or biomarkers) of the invention, such that the control or reference standard or comparator may serve as a comparator against which a sample can be compared.

By the phrase "determining the level of marker (or biomarker) expression" is meant an assessment of the degree of expression of a marker in a sample at the nucleic acid or protein level, using technology available to the skilled artisan to detect a sufficient portion of any marker expression product.

The level of a marker or biomarker "significantly" differs from the level of the marker or biomarker in a reference sample or comparator if the level of the marker in a sample from the patient differs from the level in a reference sample or comparator by an amount greater than the standard error of the assay employed to assess the marker, and preferably at least 10% or more, for example, 20%, 30%, 40%, or 50%, 60%, 70%, 80%, 90% different or more, and/or 1.1 fold, 1.2 fold, 1.4 fold, 1.6 fold, 1.8 fold, 2.0 fold different or more.

"Differentially increased expression" or "up regulation" refers to biomarker product levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween than a control.

"Differentially decreased expression" or "down regulation" refers to biomarker product levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments therebetween than a control.

A "disease" is a state of health of an animal wherein the animal cannot maintain homeostasis, and wherein if the disease is not ameliorated then the animal's health continues to deteriorate.

As used herein, an "immunoassay" refers to a biochemical test that measures the presence or concentration of a substance in a sample, such as a biological sample, using the reaction of an antibody to its cognate antigen, for example the specific binding of an antibody to a protein. Both the presence of the antigen or the amount of the antigen present can be measured.

As used herein, an "instructional material" includes a publication, a recording, a diagram, or any other medium of expression which can be used to communicate the usefulness of a component of the invention in a kit for detecting biomarkers disclosed herein. The instructional material of the kit of the invention can, for example, be affixed to a container which contains the component of the invention or be shipped together with a container which contains the component. Alternatively, the instructional material can be shipped separately from the container with the intention that the instructional material and the component be used cooperatively by the recipient.

The term "label" when used herein refers to a detectable compound or composition that is conjugated directly or indirectly to a probe to generate a "labeled" probe. The label may be detectable by itself (e.g., radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

The "level" of one or more biomarkers means the absolute amount or relative amount or concentration of the biomarker in the sample.

The term "marker (or biomarker) expression" as used herein, encompasses the transcription, translation, post-translation modification, and phenotypic manifestation of a gene, including all aspects of the transformation of information encoded in a gene into RNA or protein. By way of non-limiting example, biomarker expression includes transcription into messenger RNA (mRNA) and translation into protein, as well as transcription into types of RNA such as transfer RNA (tRNA) and ribosomal RNA (rRNA) that are not translated into protein.

The terms "microarray" and "array" refers broadly to both "DNA microarrays" and "DNA chip(s)," and encompasses all art-recognized solid supports, and all art-recognized methods for affixing nucleic acid molecules thereto or for synthesis of nucleic acids thereon. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744, 305, 5,677,195, 5,800,992, 6,040,193, 5,424,186 and Fodor et al., Science, 1991; 251:767-777, each of which is incorporated by reference in its entirety for all purposes. Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789, 162, 5,708,153, 6,040,193 and 5,800,992, which are hereby incorporated by reference in their entirety for all purposes.) Arrays may be packaged in such a manner as to allow for diagnostic use or can be an all-inclusive device; e.g., U.S. Pat. Nos. 5,856,174 and 5,922,591 incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, biomarker expression, and gene expression monitoring for a variety of eukaryotic and prokaryotic organisms. The number of probes on a solid support may be varied by changing the size of the individual features. In one embodiment the feature size is 20 by 25 microns rectangle, in other embodiments features may be, for example, 8 by 8, 5 by 5 or 3 by 3 microns rectangle, resulting in about 2,600,000, 6,600,000 or 18,000,000 individual probe features.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

A "healthy" or "normal" subject does not have any form of sc zophrenia or bipolar disorder.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

A "reference level" of a biomarker means a level of the biomarker that is indicative of a particular disease state, phenotype, or lack thereof, as well as combinations of disease states, phenotypes, or lack thereof. A "positive"

reference level of a biomarker means a level that is indicative of a particular disease state or phenotype. A "negative" reference level of a biomarker means a level that is indicative of a lack of a particular disease state or phenotype.

The term "risk stratification," according to the invention, comprises finding schizophrenic or bipolar patients, particularly those having an early or first psychotic episode, for the purpose of diagnosis and therapy/treatment of the schizophrenic or bipolar condition, with the goal of allowing as advantageous a course of the schizophrenic or bipolar condition as possible.

"Sample" or "biological sample" as used herein means a biological material isolated from a subject. The biological sample may contain any biological material suitable for detecting the desired biomarkers, and may comprise cellular and/or non-cellular material obtained from the subject. One example of a biological sample is a whole blood sample. Another example of a biological sample is a cell-free serum sample.

"Standard control value" as used herein refers to a predetermined amount of a particular protein or nucleic acid that is detectable in a contol sample. The standard control value is suitable for the use of a method of the present invention, in order for comparing the amount of a protein or nucleic acid of interest (e.g., marker, biomarker) that is present in a patient sample. An established sample serving as a standard control provides an typical amount of the protein or nucleic acid of interest in a sample type that is typical for an typical, healthy person of reasonably matched background, e.g., gender, age, ethnicity, and medical history. A standard control value may vary depending on the protein or nucleic acid of interest and the nature of the sample (e.g., whole blood, serum, etc.).

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based on the identification of biomarkers, the expression levels of which can discriminate between normal, SZ and BD subjects in a biological sample of a subject.

In one embodiment, the invention provides a combination of biomarkers for the diagnosis of SZ. In one embodiment, the invention provides a combination of biomarkers for the diagnosis of BD. In one embodiment, the invention provides a combination of biomarkers for the diagnosis of "SZ or BD." In one embodiment, the invention provides a combination of biornarkers for differentially diagnosing a subject originally diagnosed as having "SZ or BD" with "SZ" or "BD."

Identifying a Biomarker

The invention includes methods for the identification of biomarkers differentially expressed between samples of normal, SZ and BD subjects, as well as methods for the detection of the expression products of differentially expressed biomarkers of normal, SZ and BD subjects.

The invention contemplates the identification of differentially expressed biomarkers by whole genome nucleic acid microarray, to identify biomarkers differentially expressed between normal, SZ and BD subjects. The invention further contemplates using methods known to those skilled in the art to detect and to measure the level of differentially expressed biomarker expression products, such as RNA and protein, to measure the level of one or more differentially expressed biomarker expression products. In certain embodiments, the expression level of one or more regions or fragments of a gene are more informative than the expression level of the entire gene, and therefore in one embodiment, a biomarker expression product is the expression of a fragment or region of a gene.

Methods of detecting or measuring gene expression may utilize methods that focus on cellular components (cellular examination), or methods that focus on examining extracellular components (fluid examination). Because gene expression involves the ordered production of a number of different molecules, a cellular or fluid examination may be used to detect or measure a variety of molecules including RNA, protein, and a number of molecules that may be modified as a result of the protein's function. Typical diagnostic methods focusing on nucleic acids include amplification techniques such as PCR and RT-PCR (including quantitative variants), and hybridization techniques such as in situ hybridization, microarrays, blots, and others. Typical diagnostic methods focusing on proteins include binding techniques such as ELISA, immunohistochemistry, microarray and functional techniques such as enzymatic assays.

The genes identified as being differentially expressed may be assessed in a variety of nucleic acid detection assays to detect or quantify the expression level of a gene or multiple genes in a given sample. For example, traditional Northern blotting, nuclease protection, RT-PCR, microarray, and differential display methods may be used for detecting gene expression levels. Methods for assaying for mRNA include Northern blots, slot blots, dot blots, and hybridization to an ordered array of oligonucleotides. Any method for specifically and quantitatively measuring a specific protein or mRNA or DNA product can be used. However, methods and assays are most efficiently designed with array or chip hybridization-based methods for detecting the expression of a large number of genes. Any hybridization assay format may be used, including solution-based and solid support-based assay formats.

The protein products of the genes identified herein can also be assayed to determine the amount of expression. Methods for assaying for a protein include Western blot, immunoprecipitation, and radioimmunoassay. The proteins analyzed may be localized intracellularly (most commonly an application of immunohistochemistry) or extracellularly (most commonly an application of immunoassays such as ELISA).

Biological samples may be of any biological tissue or fluid. Frequently the sample will be a "clinical sample" which is a sample derived from a patient. The biological sample may contain any biological material suitable for detecting the desired biomarkers, and may comprise cellular and/or non-cellular material obtained from the subject. One example of a biological sample is a whole blood sample. Another example of a biological sample is a serum sample. Another example of a biological sample is a saliva sample. Another example of a biological sample is a urine sample.

Controls group samples may either be from a normal subject or from a subject with a known stage of SZ or BD. As described below, comparison of the expression patterns of the sample to be tested with those of the controls can be used to diagnose, or distinguish between, normal, SZ and BD subjects. In some instances, the control groups are only for the purposes of establishing initial cutoffs or thresholds for the assays of the invention. Therefore, in some instances, the systems and methods of the invention can diagnose between normal, SZ and BD subjects without the need to compare with a control group.

Methods of Differentiation and Diagnosis

The present invention relates to the identification of biomarkers associated with SZ and BD. Accordingly, the present invention features methods for identifying subjects who have developed SZ and BD, and for differentiating between SZ and BD in a subject. Subjects include those subjects who are suffering a first psychotic episode or have not yet been fully clinically characterized as having SZ or BD and subjects who have already been diagnosed as having SZ or BD. In one embodiment, the methods may be useful for identifying a subject as having a risk of developing SZ or BD. In one embodiment, the risk of SZ or BD can be assessed by measuring a combination of the biomarkers described herein, and comparing the measured values to comparator values, reference values, or index values. Such a comparison can be undertaken with mathematical algorithms or formula in order to combine information from results of multiple individual biomarkers and other parameters into a single measurement or index. Subjects identified as having an increased risk of developing SZ or BD can optionally be selected to receive treatment regimens, such as administration of prophylactic or therapeutic compounds or implementation of exercise regimens or dietary supplements to prevent, treat or delay the onset of SZ or BD.

Identifying a subject before they develop SZ or BD, or shortly after a first psychotic episode, enables the selection and initiation of various therapeutic interventions or treatment regimens in order to delay, reduce or prevent the manifestation and progression of the disorder in the subject.

The biomarkers of the present invention can thus be used to generate a biomarker profile or signature of the subjects: (i) who do not have and are not expected to develop SZ or BD and/or (ii) who have SZ or BD. The biomarker profile of a subject can be compared to a predetermined or comparator biomarker profile or reference biomarker profile to diagnose or identify subjects at risk of developing SZ or BD, to monitor the progression of the disorder, and to monitor the effectiveness of treatments. Data concerning the biomarkers of the present invention can also be combined or correlated with other data or test results, such as, without limitation, measurements of clinical parameters or other algorithms for SZ or BD. Other data includes, but is not limited to, gender, age and ethnicity. The machine-readable media can also comprise subject information such as medical history and any relevant family history.

In one embodiment, the invention is a method of diagnosing SZ. In one embodiment, the invention is a method of diagnosing BD. In one embodiment, the method includes differentiating or distinguishing between normal, SZ and BD subjects.

In various embodiments, methods are disclosed herein that may be of use to determine whether a subject has a SZ or BD. In some embodiments, these methods may utilize a biological sample (such as urine, saliva, blood, serum, amniotic fluid, or tears), for the detection of a combination of biomarkers of the invention in the sample.

In one embodiment, the method includes evaluating the expression level of a combination of biomarkers useful for distinguishing between normal, SZ and BD. In various embodiments, the combination of biomarkers is two or more biomarkers selected from the group consisting of SH3YL1, TBC1D1, TCEA3, SLC44A5, HADHA, CPA3, IL5RA, OXTR, CCDC109B, TREML4, TRIM4, PTGDS, GYLTL1B, FADS2, CRIP2, HPR, DDX5, EEF2, ZMYND8 and HLA-DRB5.

In one embodiment, the method includes evaluating the expression level of a combination of biomarkers for diagnosis of SZ. In one embodiment, the combination of biomarkers is at least two selected from the group consisting of TCEA3, SLC44A5, IL5RA, GYLTL1B and DDX5. In one embodiment, the combination of biomarkers is at least two selected from the group consisting of HPR, PTGDS, CPA3, TRIM4 and SLC44A5. In one embodiment, the combination of biomarkers is at least two selected from the group consisting of SLC44A5, CPA3, TREML4, TRIM4, PTGDS and SH3YL1.

In one embodiment, the method includes evaluating the expression level of a combination of biomarkers for the diagnosis of BD. In one embodiment, the combination of biomarkers is at least two selected from the group consisting of PTGDS, HLA-DRB5, OXTR and FADS2. In one embodiment, the combination of biomarkers is at least two selected from the group consisting of CRIP2, CPA3, OXTR, TRIM4, PTGDS and SH3YL1.

In one embodiment, the method includes evaluating the expression level of a combination of biomarkers for distinguishing a subject having SZ or BD from a healthy subject. In one embodiment, the combination of biomarkers is at least two selected from the group consisting of SLC44A5, HADHA, CPA3, OXTR, CCDC109B, TREML4, TRIM4, PTGDS, GYLTL1B, HPR and ZMYND8. In one embodiment, the combination of biomarkers is at least two selected from the group consisting of SLC44A5, CPA3, CRIP2, TRIM4, PTGDS and SH3YL1.

In one embodiment, the method includes evaluating the expression level of a combination of biomarkers for differentially diagnosing a subject identified as having "SZ or BD" as having "SZ" or "BD." In one embodiment, the combination of biomarkers is at least two selected from the group consisting of CRIP2, OXTR and FADS2. In one embodiment, the combination of biomarkers is at least two selected from the group consisting of SH3YL1, OXTR, PTGDS, CPA3, TBC1D1, and TCEA3.

In one embodiment, the method includes evaluating the expression level of a combination of biomarkers for identifying a healthy subject with respect to BD or SZ. In one embodiment, the combination of biomarkers is at least two selected from the group consisting of SLC44A5, HADHA, CPA3, OXTR, CCDC109B, TREML4, TRIM4, PTGDS, GYLTL1B, HPR and ZMYND8.

In one embodiment, the method comprises detecting a combination of biomarkers in a biological sample of the subject. In one embodiment, the biological sample is blood. In various embodiments, the level of one or more of biomarkers of the invention in the biological sample of the subject is compared with the level of the biomarker in a comparator. Non-limiting examples of comparators include, but are not limited to, a negative control, a positive control, standard control, standard value, an expected normal background value of the subject, a historical normal background value of the subject, a reference standard, a reference level, an expected normal background value of a population that the subject is a member of, or a historical normal background value of a population that the subject is a member of.

In various embodiments, the subject is a human subject, and may be of any race, sex and age. In one embodiment, the subject is a human male less than 30 years old.

Information obtained from the methods of the invention described herein can be used alone, or in combination with other information (e.g., disorder status, disorder history, vital signs, blood chemistry, etc.) from the subject or from the biological sample obtained from the subject.

In various embodiments of the methods of the invention, the level of one or more biomarkers of the invention is determined to be increased when the level of one or more of the biomarkers of the invention is increased by at least 10%, by at least 20%, by at least 30%, by at least 40%, by at least 50%, by at least 60%, by at least 70%, by at least 80%, by at least 90%, or by at least 100%, when compared to with a comparator.

In other various embodiments of the methods of the invention, the level of one or more biomarkers of the invention is determined to be decreased when the level of one or more of the biomarkers of the invention is decreased by at least 10%, by at least 20%, by at least 30%, by at least 40%, by at least 50%, by at least 60%, by at least 70%, by at least 80%, by at least 90%, or by at least 100%, when compared to with a comparator.

In the methods of the invention, a biological sample from a subject is assessed for the level of one or more of the biomarkers of the invention in the biological sample obtained from the patient. The level of one or more of the biomarkers of the invention in the biological sample can be determined by assessing the amount of polypeptide of one or more of the biomarkers of the invention in the biological sample, the amount of mRNA of one or more of the biomarkers of the invention in the biological sample, the amount of enzymatic activity of one or more of the biomarkers of the invention in the biological sample, or a combination thereof.

Detecting a Biomarker

In one embodiment, the invention includes detecting an mRNA in a bodily fluid, wherein the bodily fluid is blood and the mRNA is detected in blood. In some embodiments, detection of mRNAs is performed in a portion of a blood sample (e.g., serum).

In one embodiment, detecting mRNAs, is performed in a bodily fluid, e.g. saliva or urine, which meets the demands of an inexpensive, non-invasive and accessible bodily fluid to act as an ideal medium for investigative analysis.

Biomarkers generally can be measured and detected through a variety of assays, methods and detection systems known to one of skill in the art. Various methods include but are not limited to refractive index spectroscopy (RI), ultraviolet spectroscopy (UV), fluorescence analysis, electrochemical analysis, radiochemical analysis, near-infrared spectroscopy (near-IR), infrared (IR) spectroscopy, nuclear magnetic resonance spectroscopy (NMR), light scattering analysis (LS), mass spectrometry, pyrolysis mass spectrometry, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, colorimetry and surface plasmon resonance (such as according to systems provided by Biacore Life Sciences). See also PCT Publications WO/02004/056456 and WO/2004/088309. In this regard, biomarkers can be measured using the above-mentioned detection methods, or other methods known to the skilled artisan. Other biomarkers can be similarly detected using reagents that are specifically designed or tailored to detect them.

Different types of biomarkers and their measurements can be combined in the compositions and methods of the present invention. In various embodiments, the protein form of the biomarkers is measured. In various embodiments, the nucleic acid form of the biomarkers is measured. In exemplary embodiments, the nucleic acid form is mRNA. In various embodiments, measurements of protein biomarkers are used in conjunction with measurements of nucleic acid biomarkers.

Methods for detecting mRNA, such as RT-PCR, real time PCR, branch DNA, NASBA, RNA-Seq, digital droplet PCR, and others, are well known in the art. Using sequence information provided by the database entries for the biomarker sequences, expression of the biomarker sequences can be detected (if present) and, measured using techniques well known to one of ordinary skill in the art. For example, sequences in sequence database entries or sequences disclosed herein can be used to construct probes for detecting biomarker RNA sequences in, e.g., Northern blot hybridization analyses or methods which specifically, and, preferably, quantitatively amplify specific nucleic acid sequences. As another example, the sequences can be used to construct primers for specifically amplifying the biomarker sequences in, e.g., amplification-based detection methods such as reverse-transcription based polymerase chain reaction (RT-PCR). When alterations in gene expression are associated with gene amplification, deletion, polymorphisms and mutations, sequence comparisons in test and reference populations can be made by comparing relative amounts of the examined DNA sequences in the test and reference cell populations. In addition to Northern blot and RT-PCR, RNA can also be measured using, for example, other target amplification methods (e.g., TMA, SDA, NASBA), signal amplification methods (e.g., bDNA), nuclease protection assays, in situ hybridization and the like.

The concentration of the biomarker in a sample may be determined by any suitable assay. A suitable assay may include one or more of the following methods, an enzyme assay, an immunoassay, mass spectrometry, chromatography, electrophoresis or an antibody microarray, or any combination thereof. Thus, as would be understood by one skilled in the art, the system and methods of the invention may include any method known in the art to detect a biomarker in a sample.

The invention described herein also relates to methods for a multiplex analysis platform. In one embodiment, the method comprises an analytical method for multiplexing analytical measurements of biomarkers. In another embodiment, the method comprises a set of compatible analytical strategies for multiplex measurements of biomarkers and/or metabolites in a sample.

Evaluating Expression Level of a Biomarker

In one embodiment, the expression of a combination of biomarkers of the invention is representative of a health state and is diagnostically useful for determining the health state of a subject. One or more statistical methods, as disclosed herein, can be used to evaluate the expression level of a combination of biomarkers of the invention. Exemplary statistical methods include, for example, discriminant analysis, classification analysis, cluster analysis, analysis of variance (ANOVA), regression analysis, regression trees, decision trees, nearest neighbor algorithms, principal components, factor analysis, multidimensional scaling and other methods of dimensionality reduction, likelihood models, hypothesis testing, kernel density estimation and other smoothing techniques, cross-validation and other methods to guard against overfitting of the data, the bootstrap and other statistical resampling techniques, artificial intelligence, including artificial neural networks, machine learning, data mining, and boosting algorithms, and Bayesian analysis using prior probability distributions.

In one embodiment, a logistic regression model is used to evaluate the expression level of a combination of biomarkers of the invention. In one embodiment, a diagnostic cut-off for SZ, BD, control or a combination thereof is determined from a logistic regression model and used to diagnose a subject as having SZ, BD, "SZ or BD," or control. Due to alterations in gene expression by white blood cell counts, age and gender, and body-mass index, normative ranges may be adjusted for these covariates in logistic regression analysis.

Kits

The present invention also pertains to kits useful in the methods of the invention. Such kits comprise various combinations of components useful in any of the methods described elsewhere herein, including for example, materials for quantitatively analyzing a biomarker of the invention (e.g., polypeptide and/or nucleic acid), materials for assessing the activity of a biomarker of the invention (e.g., polypeptide and/or nucleic acid), and instructional material. For example, in one embodiment, the kit comprises components useful for the quantification of a desired nucleic acid in a biological sample. In another embodiment, the kit comprises components useful for the quantification of a desired polypeptide in a biological sample. In a further embodiment, the kit comprises components useful for the assessment of the activity (e.g., enzymatic activity, substrate binding activity, etc.) of a desired polypeptide in a biological sample.

In a further embodiment, the kit comprises components for determining the level of a combination of biomarkers of the invention in a biological sample obtained from the subject. In one embodiment, a kit is a diagnostic kit for SZ or BD and comprises at least two probes for detecting expression of at least two biomarkers selected from the group consisting of SH3 YL1, TBC1D1, TCEA3, SLC44AS, HADHA, CPA3, IL5RA, OXTR, CCDC109B, TREML4, TRIM4, PTGDS, GYLTL1B, FADS2, CRIP2, HPR, DDX5, EFF2, ZMYND8 and HLA-DRB5.

In various embodiments, the kit comprises instructional material to determine whether the level of a biomarker of the invention is modulated in a biological sample obtained from the subject, as compared with the level of at least one comparator control contained in the kit, such as a positive control, a negative control, a historical control, a historical norm, or the level of another reference molecule in the biological sample.

Treatments

In certain embodiments, treatment comprises administering a disorder-modulating treatment to a subject. In some embodiments, the disorder-modulating treatment is a drug. The drug can be a therapeutic or prophylactic used in subjects diagnosed or identified with SZ or BD, or at risk of having SZ or BD. In certain embodiments, treatment comprises modifying a therapy used in subjects diagnosed or identified with SZ or BD, or at risk of having SZ or BD. In one embodiment, modifying therapy refers to altering the drug, dosage, duration, frequency or intensity of therapy, or for example, altering the type of therapy provided to the subject.

In various embodiments, effecting a therapy comprises causing a subject to or communicating to a subject the need to make a change in lifestyle, for example, increasing exercise, changing diet, reducing or eliminating smoking, taking a drug, and so on.

In various exemplary embodiments, effecting a therapy comprises administering a disorder-modulating drug to the subject. Any drug or combination of drugs useful for treating or mediating SZ or BD may be administered to a subject on the basis of the diagnosis of SZ or BD. The drugs can be formulated in any number of ways, often according to various known formulations in the art or as disclosed or referenced herein.

In various embodiments, a drug or combination of drugs is not administered to a subject to treat a disorder. In these embodiments, the practitioner may refrain from administering the drug or combination of drugs, may recommend that the subject not be administered the drug or combination of drugs or may prevent the subject from being administered the drug or combination of drugs.

In various embodiments, one or more additional drugs may be optionally administered in addition to those that are recommended or have been administered. An additional drug will typically not be any drug that is not recommended or that should be avoided. In exemplary embodiments, one or more additional drugs comprise one or more drugs approved for the treatment or mediation of SZ or BD.

Thus, in various methods of diagnosis of the invention, the method also includes the step of administering a treatment to the subject.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Exon Array Biomarkers to Diagnose and Differentiate Schizophrenia and Bipolar Disorder Without being bound by any particular theory, it was hypothesized that for SZ and BL) there are unique and global sets of chronic differentially expressed genes in blood for each disorder. This hypothesis was based, in part, on the concept that circulating blood reflects the changing health of the body, i.e the "Sentinel Principle" (Liew et al., J Lab Clin Med 2006; 147(3): 126-132). As blood circulates through the brain, communication occurs between cells in blood and the brain (Weber et al., Neuropsychopharmacology 2017; 42(1): 46-61). Following a brain injury, neutrophils, macrophages, lymphocytes, and dendritic cells can extravasate into the brain from the blood (Gelderblom et al., Stroke 2009; 40(5): 1849-1857). These extravasated cells can induce changes in gene expression and protein as reported in neuroimmune studies (Downes and Crack, Br J Pharmacol 2010; 160(8): 1872-1888; Brea et al., Cerebrovasc Dis 2009; 27 Suppl 1: 48-64). In prior work using blood-brain samples from the same subjects, about 20% of the transcriptome was expressed at comparable levels and significantly correlated in both tissues from the same subjects (Rollins et al., Am J Med Genet B Neuropsychiatr Genet 2010; 153B(4): 919-936). This correlation supports the idea that important biomarkers of either SZ or BD could be expressed peripherally, and these would also have a connection to the central modulation of neuroimmune responses. Advantages of a peripheral transcriptomics study are the ease of access to whole blood and the fact that immune genes are highly expressed. For example, multiple HLA region genes with genome-wide significance are expressed in peripheral blood samples, such as C4 (Sekar et al., Nature 2016; 530(7589): 177-183) and HLA-DPA1 (Morgan et al., Microarrays (Basel) 2016; 5(1)).

To date, there are no validated biomarker studies of schizophrenia or bipolar disorder using peripheral blood gene expression, although a number of serum proteins have been advanced as validated biomarkers (Chan et al., Prog Neurobiol 2014; 122: 45-72; Chan et al., Transl Psychiatry 2015; 5: e601; Haenisch et al., Brain Behav Immun 2016; 52: 49-57; Scarr et at, Int J Neuropsychopharmacol 2015; 18(10): pyv042; Tomasik et al., Eur Arch Psychiatry Clin Neurosci 2012; 262 Suppl 2: 579-83). A recent mega-analysis of blood samples comparing SZ and controls was conducted with a total of 578 subjects in nine studies. The mega-analysis of blood transcriptome, showed that 220 genes reached a Bonferroni-corrected level of significance (Hess et al., Schizophr Res 2016; 176(2-3): 114-124), indicating the utility of analysis of blood transcriptome for finding differentially expressed genes. There is little agreement among researchers of which mRNA and protein are jointly dysregulated in the blood of neuropsychiatric patients leaving open the question of which are the most important genes and proteins still to be explored (Sanders et at., Hum Mol Genet 2013; 22(24): 5001-5014; Hess et al., Schizophr Res 2016; 176(2-3): 114-124; Glatt et al., Curr Pharmacogenomics Person Med 2009; 7(3): 164-188; Glatt et al., Am J Med Genet B Neuropsychiatr Genet 2011; 156B(8): 869-887; Horvath and Mimics, Biol Psychiatry 2014; 75(4): 316-323; Kumarasinghe et al., Int J Neuropsychopharmacol 2013; 16(7): 1483-1503; Wu et al., Brain Behav Immun 2016; 53: 194-206; Xu et al., Sci Rep 2016; 6: 16767; Martin et al., BMC Med Genomics 2009; 2: 62; Vawter et al., Brief Funct Genomics 2011; 10(6): 387-399; Manidani et at, Dis Markers 2013; 35(1): 11-21). The stability of this potential dysregulation has not been tested across illness progression.

The objective of the present study is to test subjects at multiple time points by enrolling SZ (n=30), BD (n=30), and normal control (NC; n=30) subjects at one clinical site to eliminate potential sources of variation. The expression levels of panels of genes were used to define which disorder the patient was diagnosed with the highest likelihood. Tempus Blood RNA tubes and Affymetrix exon arrays were previously validated in a study that measured the sources of variation for 8 healthy controls at 9 sequential blood draws every 6 hours (Rollins et al., Am J Med Genet B Neuropsychiatr Genet 2010; 153B(4): 919-936). The resulting data showed that about 20% of the transcripts measured on the Affymetrix exon array did not significantly change over 9 blood draws (Rollins et al., Am J Med Genet 13 Neuropsychiatr Genet 2010; 153B(4): 919-936). The remaining 80% of transcripts were changed significantly during this experiment (Rollins et al., Am J Med Genet B Neuropsychiatr Genet 2010; 153B(4): 919-936). Taken together, it is expected that 20% of transcripts will be stable over longer periods of time and do not significantly fluctuate by time of day of the blood draw. This data reinforces the purpose of the present study to test whether stable expression of genes occurs over months instead of days that can be used as a biomarker for SZ and BD to differentiate from controls. In this study RNA expression was measured with the Affymetrix exon array 1.0 ST for biomarker screening. Exon arrays have been widely used for the study of genetic variation in coding regions (Bemmo et al., BMC Genomics 2008; 9: 529; Benovoy et al., Nucleic Acids Res 2008; 36(13): 4417-4423; Duan et al., Bioinformation 2008; 2(10): 469-470; Heinzen et al., PLoS Biol 2008; 6(12): el.; Kwan et al., Nat Genet 2008; 40(2): 225-231; Sequeira et al., Mol Psychiatry 2008; 13(4): 363-365; Duan et al, Pharmacogenomics 2009; 10(4): 549-563; Fraser and Xie, Genome Res 2009; 19(4): 567-575; Martin et al., BMC Med Genomics 2009; 2: 62; Gamazon et al., PLoS One 2010; 5(2): e9366; Gamazon et al., Bioinforinatics 2010; 26(2): 259-262; Pradervand et al., BioTechniques 2008; 44(6): 759-762). Exon array findings correlate positively with RNA-Sell across most levels of transcript expression (Agarwal et al., BMC Genomics 2010; 11: 383), and in some cases have less false-positive detection than RNA-Seq (Bradford et al., BMC Genomics 2010; 11: 282; Liu et al., Nucleic Acids Res 2011; 39(2):578-88; Richard et al., Nucleic Acids Res 2010; 38(10): e112). The analytical techniques for the exon arrays have been well established (Kapur et al., Bioinformatics 2008; 24(24): 2887-2893; Kapur et al., Genome Biol 2007; 8(5): R82; Xing et al., PLoS One 2006; 1: e88; Xing et al., Mol Biol Evol 2007; 24(6): 1283-1285; Xing et al., RNA 2008; 14(8): 1470-1479; Lin et al., Nucleic Acids Res 2009; 37(12): e90; Shen et al., Bioinformatics 2010; 26(2): 268-269; Liu et al., Nucleic Acids Res 2011; 39(2): 578-588).

To determine stable temporal biomarkers, this study evaluated whole blood gene expression at two different time points using the same subjects to differentiate schizophrenia, bipolar disorder type I, and controls. The diagnostic algorithm uses logistic regression modeling and a total of 18 unique expressed exons within known mRNA transcripts. The model discriminated schizophrenia and bipolar disorder from each other, as well as both from healthy controls in four steps. The upper limit of accuracy achieved in this study was 88%, using the same patients, gene expression platform, and biomarker panel. It is expected that application of these panels to first-episode or prodromal subjects may improve the prediction for those subjects that ultimately convert to either illness. This will require an additional validation study of the biomarker signatures with a larger cohort size, which was estimated using a power analysis as 310 subjects in a follow-on project for prediction of first-episode or prodromal patients.

The expression differences of three genes related to polyunsaturated fatty acids (PUFAs) and prostaglandin biosynthesis was used in the final biomarker panels to differentiate schizophrenia, bipolar disorder, and controls (PTGDS, FADS2, HADHA), Previously these genes have been associated in psychiatric disorders such as bipolar disorder, major affective disorder, schizophrenia, and anxiety. PTGDS is involved in synthesis of PGD2 from PGH2, the cyclooxygenase-mediated product of arachidonic acid which is a PUFA (Begemann et al., Mol Med 2008; 14(9-10): 546-552). PTGDS is a top anxiety gene modulated by changes in PUFA (omega-3 fatty acid docosahexaenoic acid) (Le-Niculescu et al., Transl Psychiatry 2011; 1: e9) on the convergent functional genomics scale. Increased expression of FADS2 has been found in schizophrenia and bipolar disorder postmortem brain (Liu and McNamara, Psychiatr Res 2011; 45(2): 269-272; Liu et al., Schizophr Res 2009; 109(1-3): 113-120). FADS2 activity was increased in bipolar disorder and was associated with suicidal behavior (Evans et al., PLoS One 2012; 7(1): e29297). In the present study increased expression of FADS2 was found in bipolar disorder, in agreement with FADS2 findings reported. The increased activity of FADS2 could reduce PUFA levels of both AA and EPA by promoting conversion to longer chain fatty acids. Thus studies of PUFA supplementation in mood disorder with n-3 fatty acids was effective in 4 out of 7 well controlled studies in reducing mood symptoms (Evans et al., PLoS One 2012; 7(1): e29297). The expression data for FADS2, while interesting, could be subject to dietary influence, such as amounts and types of daily dietary intake of fatty acids, timing of intake, and also medication effects on these genes. Further, genetics plays a significant role, especially in modulating levels of fatty acids and FADS2 expression.

From GWAS of schizophrenia and bipolar disorder, there is a large number of variants contributing to the polygenic susceptibility for these disorders. It is likely that we have highlighted several genes that contribute towards this susceptibility using transcription analysis, as some but not all polygenic effects such as expression quantitative trait loci might be consistent across blood and brain (Vawter et al., Brief Funct Genomics 2011; 10(6): 387-399; Mamdani et al., Dis Markers 2013; 35(1): 11-21) Additionally two upstream transcription factor merit further investigation, MKL2 and REL, which appear to oppositely regulate genes in BD and SZ, resulting in the ability to differentially diagnose these subjects. These proto-oncogenes have not been previously associated with psychiatric disorders, There was a consistent increase in expression of IL5RA (interleukin 5 receptor, alpha) in lithium treated subjects with bipolar disorder in PBMCs that passed strict FDR (Anand et al., Mol Neuropsychiatry 2016; 2(3): 115-123). In the final biomarker panel, a trend for an increase in IL5RA expression in BD (p-value for BD was 0.056 and fold change was 1.16) was found, however IL5RA expression in SZ was significantly decreased and passing FDR (p-value for SZ vs. NC, 2.65E-08, fold change −1.59). For PLB1 (phospholipase B1), in PBMC, lithium decreased expression (−1.17 fold change) passing FDR 82 in PBMCs, while in the present study, PLB1 was significantly decreased in BD by −1.19 and was not significantly increased in SZ (p=0.06, fold change 1.16). It is unlikely that some expression in the biomarker panel might be due to lithium treatments, since only 2 BD subject were lithium-treated in this study. Another ramification of using biomarkers is to provide a method to monitor drug efficacy and other appropriate early psychosocial interventions for mental disorders. In a separate analysis, the phenotypic neuropsychiatric ratings data obtained from each patient are correlated with the gene expression data.

Over 100,000 adolescent Americans suffer from symptoms of psychosis each year and, currently, there are no biomarkers tests that are FDA approved to classify SZ or BD. There is a need for an 'objective' clinical laboratory test for an early diagnosis of these mental disorders since these disorders may take months or even years to arrive at a diagnosis and for patients to receive effective treatments. The lag in treatment is associated with an increase in the suicide rate and recurrent episodes of psychosis and mood dysregulation. There is a large increase in deaths reported in first episode psychosis subjects due to lack of treatment after the first year of illness (Schoenbaum, Twelve-Month Health Care Use and Mortality in Commercially Insured Young People With Incident Psychosis in the United States. Schizophrenia Bulletin 2017). Thus, it is imperative to have objective biomarkers to help implement treatment at an early stage. One estimate of the direct and indirect annual costs in the USA for schizophrenia is $174 billion (Cloutier et al., J Clin Psychiatry 2016; 77(6): 764-771) plus additional cost of $151 billion for bipolar disorder (Dilsaver, J Affect Disord 2011; 129(1-3): 79-83). The biomarker signatures could lead to faster and more accurate diagnoses, reducing the duration of untreated psychosis, reduction in suicidality, reduction in cognitive decline and add to the understanding of shared and unique pathophysiologies of each disorder. The blood test results that are described offer molecular diagnostic support for a psychiatrist's clinical evaluation with rapid clinical laboratory test results.

The materials and methods employed in these experiments are now described.

Subject Enrollment

Subject enrollment occurred at a single clinical site at the University of Iowa in an institutional review board (IRB) approved study. Chronic SZ and BD type I outpatients ages 18-45, provided consent for the study. All subjects met DSM-IV-R criteria and completed the study: SZ (n=30), BD (n=30), and NC (n=30). Clinical assessments included the Scale for the Assessment of Positive Symptoms and Scale for the Assessment of Negative Symptoms (SAPS, SANS), medications and drugs for SZ and BD subjects; Young Mania Rating Scale (YMRS), and Hamilton Rating Scale for Depression (HAM-D or HRSD) for BD subjects. This neuropsychiatric assessment data will be analyzed and reported separately for state biomarker relationships. A mental status exam for normal controls (NC) consisted of the Mini-Mental Status Exam. The outline of the study is shown in FIG. 1.

Whole blood samples were collected in Tempus Blood RNA tubes (Applied Biosystems) from SZ, BD, and NC subjects at 3 visits spanning 3 months. For this report, Tempus tubes from visits 2 and 4 were extracted and RNA gene expression was measured using Affymetrix exon arrays for both visits on all 90 subjects. High-quality RNA was extracted from the Tempus tubes using the manufacturer's protocol and quality was assessed on an Agilent Bioanalyzer using RNA Integrity Number (RIN).

Human Exon Array for Biomarker Profile

There are advantages to using the Affymetrix exon arrays (Xu et al., Proc Natl Acad Sci USA 2011; 108(9): 3707-3712) compared to whole transcriptome shotgun sequencing (RNA-Seq). At the time of sample collection, the cost factor was favorable for future clinical biomarker trials that would require hundreds of arrays compared to the cost of RNA-Seq for the entire validation. The processing time and data storage requirements are more favorable for a study this size using exon arrays. Although, previous studies have found that SNPs can affect probe hybridization and consequently alter expression (Benovoy et al., Nucleic Acids Res 2008; 36(13): 4417-4423; Fraser and Xie, Genome Res 2009; 19(4): 567-575; Gamazon et al, PLoS One 2010; 5(2): e9366; Gamazon et al., Bioinformatics 2010; 26(2): 259-262; Duan et al., Am J Hum Genet 2008; 82(5): 1101-1113), those probesets with common SNPs were eliminated from the final dataset. The exon arrays were run at the Functional Genomics Laboratory, University of California, using the manufacturer's protocol (Affymetrix, Santa Clara, CA). The Functional Genomics Laboratory has run over 1,000 Affymetrix arrays with high-quality call rates.

Data Analysis

The Affymetrix exon array GEL files were imported into Partek Genomics using batch effect removal. The batch effect was based upon exon array scan dates as usually 12 arrays were scanned in a single day. The mean intensity of probes was summarized at the probeset level. Probesets containing common SNPs were excluded from the import and downstream analysis. The resulting probesets were then median centered within each exon array sample individually (n=180). A two-factor ANOVA was run for each probeset, using diagnosis, visit, and diagnosis x visit interaction. A false discovery rate of $6 \times 10^{-8}$ was established for diagnosis effect based upon 835,000 probesets. Three filters were used to select probesets from the ANOVA results that passed FDR for diagnosis and were in the most significant p-values for BD compared to NC, BD compared to SZ, and SZ compared to NC. The resulting list of top probesets was filtered to reveal probesets mapping to known RefSeq genes. These probesets were ranked, and the top 300 probesets were evaluated for biomarker signature.

Biomarker Signature

The modeling proceeded in four steps to select the most predictive panel of probesets out of the top 300 in each step for discriminating between groups:
Step 1: NC vs, BD+SZ
Step 2: NC vs. SZ
Step 3: NC vs. BD
Step 4: SZ vs. BD Multivariate logistic regression modeling with forward stepwise selection (SAS PROC LOGISTIC) was used on the combined visit 2 and 4 data from the groups included in the step to select the probesets that were most discriminating between the groups. A probeset was added into the model if the estimate was the most significant with p<0.001 and the resulting ROC AUC also retained statistical significance. Forward selection stopped when potential probesets were no longer statistically significant or did not appreciably improve the ROC AUC. Processing for each step resulted in a subset of the 300 probesets where each probeset contributed to the model significantly and the panel represented the smallest number of probesets that had very high diagnostic utility based on the ROC AUC.

Modeling for the diagnostic for each step was applied to the Visit 2 data using the identified probesets. The optimal cut-point for discriminating between the groups based on the logistic model prediction was obtained by maximizing the Youden Index J 76, where J=True Positive Rate (TPR)-False Positive Rate (FPR). The Visit 2 prediction model was then applied to the Visit 4 data to assess utility for a second set of data which included stability over time.

Further validation for each of the four panels included "leave one out" cross-validation where one subject was sequentially left out of the logistic model fit using the remaining subjects and then the predictability of the model for the excluded subject was assessed.

Quantitative PCR

Transcripts were selected for qPCR validation based upon significant differences using the ANOVA-filter. Three filters were used to select probesets that represented a combination of the most significant ANOVA p-values for BD compared to NC, BD compared to SZ, and SZ compared to NC. Standard SybrGreen qPCR methods previously described by the Functional Genomics Laboratory (UC Irvine) were used to confirm gene expression derived from the exon array dataset (Morgan et al., Microarrays (Basel) 2016; 5(1)).

NanoString Gene Expression Platform

A non-PCR based approach of measuring RNA as technical validation of the findings was used based upon NanoString technology (NanoString, Seattle, WA) (Mamdani et al., Transl Psychiatry 2015; 5: e636). The Nanostring platform requires a small quantity of RNA and provides digital counts of hybridization of mRNA to targets. The NanoString multiplex assay uses 100 ng of total RNA and all of the RNA samples were processed at the UCI Genomics High-Throughput Facility. A total of 50 target genes were selected for technical validation, including 44 custom Nanostring probes designed to match the closest probeset on the Affymetrix exon array that was in the biomarker panel, and 6 Nanostring probes for housekeeping genes. The resulting NanoString data was processed according to manufacturer's suggested protocol as outlined. Each data point was preprocessed by the six positive controls, the eight negative controls and the five housekeeping genes as follows: i) Calculate for each subject/visit, the sum of the positive controls, the mean of the negative controls, and the sum of the housekeeping genes. ii) Calculate across all subjects/visits, the mean of the positive control sums, and the mean of the housekeeping gene sums. iii) For each subject/visit, multiply the data point by (sum of positive controls/mean of positive control sums), subtract off the mean of the negative controls, divide by (sum of housekeeping genes/mean of housekeeping gene sums). If the normalized data point was negative, it was set to zero. The normalized Nanostring data were then analyzed for diagnostic accuracy using a model fitting approach. A potential gene probe set was selected by including all probe sets that had p<0.1 in a univariate logistic regression fit of the probe set on at least one of the diagnosis comparisons (NC vs (SZ+BD), NC vs SZ, NC vs BD, SZ vs BD) for the visit 2data.

The Results of the Experiments are Now Described

The top 300 probesets from the Affymetrix exon microarray based upon ANOVA significance were evaluated for biomarker signature (as described in Methods) for differentiating BD, SZ, and NC subjects. The resulting biomarker signature was composed of 23 probesets that condensed into 18 known RefSeq genes (biomarker panel Table 1). The diagnostic logistic model was built in four steps, using Visit 2 transcripts shown in Table 1. The resulting logistic predictive model based on Visit 2 was then applied to the Visit 4 data. The summary of individual steps in the construction of the biomarker gene panels are shown (Table 2).

TABLE 1

Probesets that were found to reliably discriminate BD, SZ, and NC were assigned to known RefSeq transcripts.

| Biomarker Panel (Comparisons) | Affymetrix Exon Microarray Transcript ID | Gene |
|---|---|---|
| BD-NC | 2661992 | OXTR |
| BD-NC | 3195034 | PTGDS |
| BD-NC | 3333247 | FADS2 |
| BD-NC | 4048241 | HLA-DRB5 |
| BD-SZ | 2661992 | OXTR |
| BD-SZ | 3333247 | FADS2 |
| BD-SZ | 3554818 | CRIP2 |
| BD-SZ-NC | 2418570 | SLC44A5 |
| BD-SZ-NC | 2545092 | HADHA |
| BD-SZ-NC | 2647109 | CPA3 |
| BD-SZ-NC | 2661992 | OXTR |
| BD-SZ-NC | 2739160 | CCDC109B |
| BD-SZ-NC | 2906720 | TREML4 |
| BD-SZ-NC | 3063536 | TRIM4 |
| BD-SZ-NC | 3195034 | PTGDS |
| BD-SZ-NC | 3667890 | HPR |
| BD-SZ-NC | 3846538 | EEF2 |
| BD-SZ-NC | 3908149 | ZMYND8 |
| SZ-NC | 2401347 | TCEA3 |
| SZ-NC | 2418570 | SLC44A5 |
| SZ-NC | 2660617 | IL5RA |
| SZ-NC | 3329099 | GYLTL1B |
| SZ-NC | 3766893 | DDX5 |

The diagnostics algorithm uses a four step decision model: Step 1, BD and SZ vs. NC; Step 2, SZ vs. NC; Step 3, BD vs. NC; and Step 4, SZ vs. BD (Table 2).

TABLE 2

Prediction model trained on Visit 2 and then applied to Visit 4. The confusion matrices show the numbers of subjects correctly and incorrectly classified for each iteration of the classification.

|  | Step 1 SZ & BD | | Step 2 | | Step 3 | | Step 4 | | Final Call | | |
|---|---|---|---|---|---|---|---|---|---|---|---|
| Actual | NC | BD | NC | SZ | NC | BD | SZ | BD | NC | SZ | BD |
| Training Visit 2 | | | | | | | | | | | |
| 30 NC | 30 | 0 | 24 | 6 | 26 | 4 | | | 21 | 5 | 4 |
| 30 SZ | 3 | 27 | 1 | 29 | | | 29 | 1 | 3 | 26 | 1 |
| 30 BD | 1 | 29 | | | 1 | 29 | 1 | 29 | 1 | 1 | 28 |
| Testing Visit 4 | | | | | | | | | | | |
| 30 NC | 28 | 2 | 23 | 7 | 28 | 2 | | | 22 | 6 | 2 |
| 30 SZ | 1 | 29 | 0 | 30 | | | 29 | 1 | 1 | 28 | 1 |
| 30 BD | 1 | 29 | | | 0 | 30 | 0 | 30 | 1 | 0 | 29 |

Step 1: 11 gene diagnostic differentiating BD + SZ vs. NC
Step 2: 5 gene diagnostic differentiating SZ vs. NC
Step 3: 4 gene diagnostic differentiating BD vs. NC
Step 4: 3 gene diagnostic differentiating SZ vs. BD
Final Call: Summary of Steps 1, 2, 3, and 4 classifications.

TABLE 3

The overall results show a stable clinical biomarker signature of mRNA expression across a 90-day test-retesting period with an accuracy of 88% on the retesting data.

|  | Visit 2 Actual | | | Visit 4 Actual | | | Both Actual | | |
|---|---|---|---|---|---|---|---|---|---|
| Predicted | BD | SZ | NC | BD | SZ | NC | BD | SZ | NC |
| BD | 28 | 1 | 4 | 29 | 1 | 2 | 57 | 2 | 6 |
| SZ | 1 | 26 | 5 | 0 | 28 | 6 | 1 | 54 | 11 |
| NC | 1 | 3 | 21 | 1 | 1 | 22 | 2 | 4 | 43 |
| Accuracy | | 83% | | | 88% | | | 86% | |
| Sensitivity (SZ) | | 87% | | | 93% | | | 90% | |
| Sensitivity (BD) | | 93% | | | 97% | | | 95% | |
| Specificity (NC) | | 70% | | | 73% | | | 72% | |

The 18-gene biomarker panels, using logistic regression modeling, correctly differentiated the three groups of subjects: SZ (n=30), BD type I (n=30) and NC (n=30) with high accuracy at Visit 2 and Visit 4. The Visit 2 mRNA biomarker levels were significantly correlated with Visit 4 levels (p<0.0001) showing temporal stability.

The initial model was developed for selecting stable probesets across visits and incorporated all subjects and visits to select the most informative probesets. To test that no single subject was overly influential in determining the model, the initial probesets were evaluated in a "leave one out" method, whereby a new model is fit to the remaining subjects, and the left out subject is identified. "Leave one out" cross validation is a model validation technique for assessing how the results of a statistical analysis will generalize to an independent data set. It is mainly used in settings where the goal is prediction to estimate how accurately a predictive model will perform in practice. This cross validation was applied to the Visit 2 data from each of the four probeset panels (Table 4).

TABLE 4

The overall results fitting a leave-one out validation model to remaining subjects show a stable clinical biomarker signature of mRNA expression across a 90-day test-retesting period with an accuracy greater than 87% on the retesting data at each of the model classification steps.

|  | BD & SZ vs. NC 11-Gene Panel | SZ vs. NC 5-Gene Panel | BD vs. NC 4-Gene Panel | SZ vs. BD 3-Gene Panel |
|---|---|---|---|---|
| Actual Visit 2 Data | | | | |
| Sensitivity (SZ) | 93% | 97% |  | 97% |
| Sensitivity (BD) | 93% |  | 97% | 97% |
| Specificity (NC) | 100% | 80% | 87% |  |
| Accuracy | 96% | 88% | 92% | 97% |
| Leave One Out X-Validation | | | | |
| Sensitivity (SZ) | 90% | 93% |  | 90% |
| Sensitivity (BD) | 90% |  | 93% | 93% |
| Specificity (NC) | 83% | 80% | 80% |  |
| Accuracy | 88% | 87% | 87% | 92% |

The results are very consistent between the actual data and the "leave one out" analyses indicating that the models should be predictive as applied to independent data cohorts (Table 4).

The area under the curve for each step was greater than 0.95, which is an indication of high combined sensitivity and specificity of classification into three groups (Table 5). When analyzing the same 1.8-gene biomarker panel and including the white blood cell counts as a covariate, the analysis slightly improved the diagnostic predictability of the SZ vs. NC, and BD and SZ vs. NC.

TABLE 5

The diagnostic algorithm uses four individual steps, shown in each column.

| BD & SZ vs. NC | SZ vs. NC | BD vs. NC | SZ vs. BD |
|---|---|---|---|
| 11-Gene Panel | 5-Gene Panel | 4-Gene Panel | 3-Gene Panel |
| *AUC = 0.994 | AUC = 0.954 | AUC = 0.974 | AUC = 0.998 |
| (p < 0.0001) | (p < 0.0001) | (p < 0.0001) | (p < 0 .0001) |

*area under the curve (AUC) of the receiver operating characteristic (ROC)

To account for potential medication effects (since many of the SZ and BD subjects were on stable dosages of antipsychotic or mood stabilizer medications at the time of blood draw) the possibility that these medications could drive some of the differential transcription signatures was analyzed. A subset of non-medicated BD (n=3) and SZ (n=1) cases were analyzed using the 18-gene diagnostics, which produced 100% accuracy in these four cases. In addition, to test this possible explanation of the gene signature, an even larger cohort of antipsychotic-free SZ patients was re-analyzed using the Illumina gene expression microarray datasets (de Song et al., PLoS One 2012; 7(6): e39498). The genome-wide RNA expression profiling was obtained with the Elumina HumanRef-8 V3 arrays for batch 1 and Human-Ref-12 V3 arrays for batch 2 using Illumina's standard protocol at UCLA's Elumina facility. The raw microarray data were available at gene expression omnibus (GEO) under accession GSE38485. Dataset includes schizophrenia patients on antipsychotic-free (n=15) and healthy controls (n=22). The 18 gene signature was extracted from the Illumina dataset and analyzed by the same logistic regression equations derived from the fit to the original data. Using this independent Illumina dataset of gene expression data from antipsychotic-free SZ subjects, the 18-gene diagnostics produced a ROC accuracy of 0.866 in patients less than 30 years of age and medication free (Table 6). These results were achieved with different gene expression technology, different blood collection tubes, and different mRNA extractions technique. The details on the methods and analysis of the antipsychotic-free patients are in Example 8.

TABLE 6

The 18 gene signature was extracted from an independent dataset of gene expression and analyzed by the same logistic regression equations derived from the fit to the original data. Using this datasetfrom antipsychotic-free SZ subjects, the 18-gene diagnostics produced a ROC accuracy of 0.866 in patients less than 30 years of age and medication free. Classification of Antipsychotic free patients with SZ using data from Illumina HT-8 array

| Subjects | NC (N) | SZ (N) | ROC AUC | Sensitivity | Specificity |
|---|---|---|---|---|---|
| Antipsychotic-free, all subjects | 22 | 15 | 0.642 | 80.00% | 59.10% |
| Antipsychotic-free, subjects ages <30 | 14 | 8 | 0.866 | 100.00% | 71.40% |

QPCR Validation of Exon Array

Transcripts were validated for schizophrenia and controls using qPCR. Those selected transcripts are shown in Table 7.

TABLE 7

QPCR results for candidate gene expression differences in schizophrenia and controls.

| Exon Array | p-value (SZ vs. NC) | Ratio (SZ vs. NC) | qPCR | p-value (SZ vs. NC) | Ratio (SZ vs. NC) |
|---|---|---|---|---|---|
| Gene Symbol | | | | | |
| EDIL3 | 1.04E−13 | 0.446 | ED1L3 | 0.01418 | 0.425 |
| NRCAM | 1.37E−02 | 0.525 | NRCAM | 0.06127 | 0.663 |
| PTGDS | 1.41E−14 | 0.722 | PTGDS | 0.04731 | 0.695 |
| DSC2 | 6.86E−04 | 1.592 | DSC2 | 0.00005 | 2.021 |
| NRG1 | 1.14E−02 | 2.062 | NRG1 | 0.01021 | 1.979 |
| ITGA2B | 3.71E−02 | 2.088 | ITGA2B | 0.00007 | 2.269 |
| ITGB3 | 2.65E−02 | 2.601 | ITGB3 | 0.00005 | 2.065 |

Figure 2:
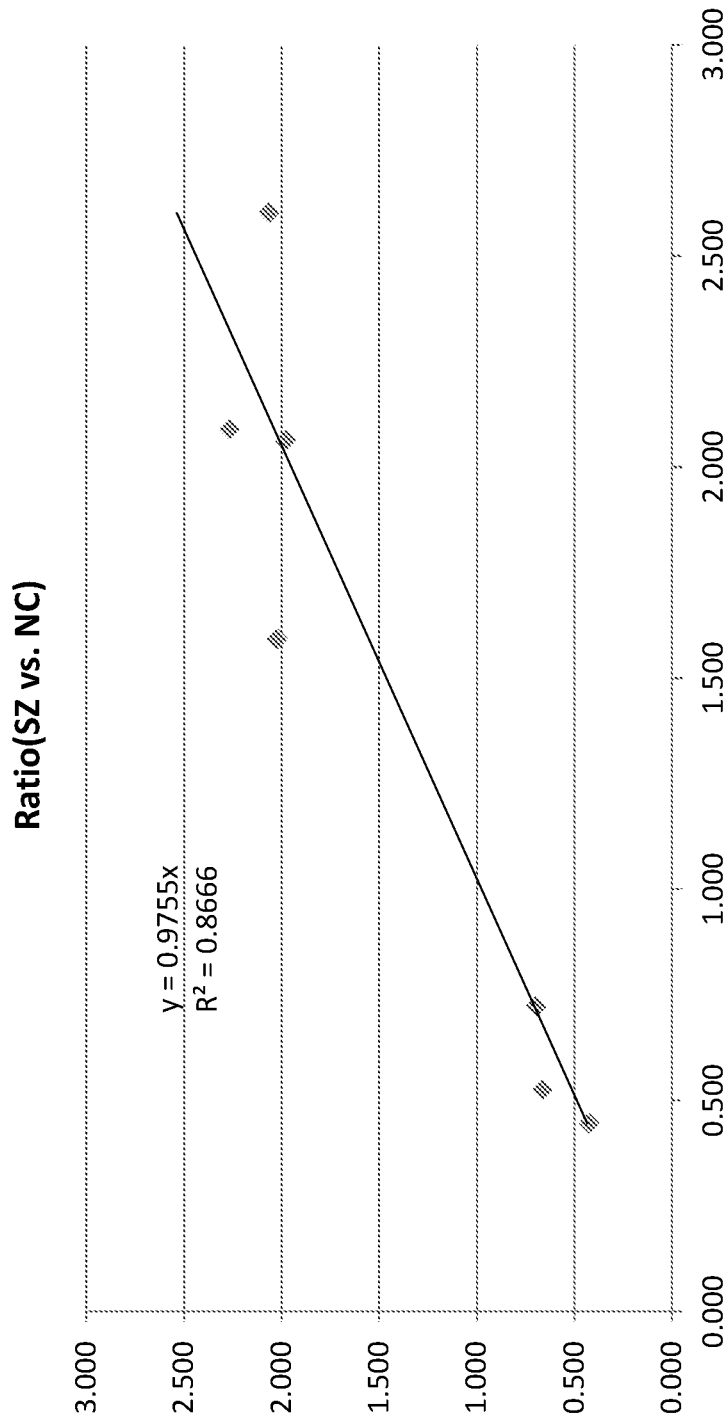
FIG. 2 depicts the results of exemplary experiments demonstrating the fold change ratio (SZ compared to normal control (NC)) for exon microarray results as compared to fold change ratio (SZ compared to NC) of qPCR.

The fold change ratio (SZ compared to NC) for exon microarray results were compared to fold change ratio (SZ compared to NC) of qPCR. The fold changes were highly correlated (FIG. 2).

Nanostring Platform Accuracy for Diagnostic Classification

TABLE 8

The Nanostring data set was analyzed by ANOVA, and the following 23 probe sets representing 11 genes passed the initial ANOVA filter ($p < 0.1$).
11 genes passed the initial ANOVA using Nanostring

| | | | |
|---|---|---|---|
| *2537112_SH3YL1 (30) | 3554838_CRIP2 (39) | 2661997_OXTR (43) | 2723770_TBC1D1 (55) |
| 2537128_SH3YL1 (61) | 3554839_CRIP2 (58) | 2906726_TREML4 (45) | 4048243_HLA-DRB5 (57) |
| 2647127_CPA3 (35) | 3554833_CRIP2 (68) | 2906736_TREML4 (50) | 3195045_PTGDS (59) |
| 2647122_CPA3 (47) | 2418615_SLC44A5 (40) | 2906735_TREML4 (53) | 2401364_TCEA3 (64) |

TABLE 8-continued

The Nanostring data set was analyzed by ANOVA, and the following 23 probe sets representing 11 genes passed the initial ANOVA filter (p < 0.1). 11 genes passed the initial ANOVA using Nanostring

| | | | |
|---|---|---|---|
| 2647124_CPA3 (65) | 2418581_SLC44A5 (46) | 2906733_TREML4 (62) | 2401362_TCEA3 (70) |
| 2647119_CPA3 (69) | 2418590_SLC44A5 (51) | 3063538_TRIM4 (52) | |

*Format is Affymetrix Exon Array Probeset ID_Gene Symbol_Variable Number Entered Into Regression For Nanostring data, the best multivariate logistic regression model for diagnosis at visit 2 was obtained by stepwise backward elimination from the full 23 probe set multivariate model to a reduced model with all included probe sets significant with p<0.05 or p<0.1 to maintain AUC>0.9. The cut point for each reduced diagnostic model was found which optimized both sensitivity and specificity based on the visit 2 data, this reduced the useful probe set number to 12 (Table 9). The diagnostic model and cut point were then applied to the visit 4 data to estimate the visit 4 sensitivity and specificity and the agreement between the visit 2 and visit 4 diagnostic predictions.

TABLE 9

Summary of Nanostring Cut Point Diagnostic Accuracy

| | NC vs SZ/BD | NC vs SZ | NC vs BD | SZ vs BD |
|---|---|---|---|---|
| Sig Probe sets | | | | |
| 2537112_SH3YL1 (30) | x | X | x | x |
| 2537128_SH3YL1 (61) | | X | x | x |
| 2647124_CPA3 (65) | x | X | x | x |
| 2647119_CPA3 (69) | x | X | x | x |
| 3554833_CRIP2 (68) | x | | x | |
| 2418590_SLC44A5 (51) | x | x | | |
| 2661997_OXTR (43) | | | x | x |
| 2906733_TREML4 (62) | | x | | |
| 3063538_TRIM4 (52) | x | x | x | |
| 2723770_TBC1D1 (55) | | | | x |
| 3195045_PTGDS (59) | x | x | x | x |
| 2401362_TCEA3 (70) | | | | x |
| AUC | 0.913 | 0.990 | 0.953 | 0.905 |
| Visit 2 Sensitivity | 98.3% | 96.6% | 89.3% | 86.2% |
| Visit 2 Specificity | 75.0% | 96.4% | 92.9% | 82.1% |
| Visit 4 Sensitivity | 87.5% | 75.0% | 75.0% | 57.1% |
| Visit 4 Specificity | 60.0% | 80.0% | 76.0% | 85.7% |
| Visit 2 4 Agreement | 77.6% | 76.0% | 75.5% | 64.2% |

Comparison of Affymetrix Exon Array and Nanostring Results

The prediction accuracies for diagnosis were compared between the Affymetrix exon array and Nanostring platform. In general, for the exon array, the model performed equally well for Visit 2 and Visit 4 data due to the data driving the selection algorithm from the original platform. The Visit 2 and Visit 4 agreement for the Affymetrix exon array was significantly higher than Nanostring reproducibility diagnosis classification (two tailed paired t-test, p=0.046). These results show that the test-retest reproducibility of the algorithm using the same subjects was best when using the original platform.

TABLE 10

Comparison of Affymetrix and Nanostring results showed that Affymetrix exon array had higher sensitivity and specificity for prediction.

| | Genes Included in Each Predictive Model | | | | | | | |
|---|---|---|---|---|---|---|---|---|
| Nanostring | NC vs SZ/BD | | NC vs SZ | | NC vs BD | | SZ vs BD | |
| Probe Set IDs | Affy ID | Nanostring | Affy ID | Nanostring | Affy ID | Nanostring | Affy ID | Nanostring |
| 2537112_SH3YL1 (30) | | x | | x | | x | | x |
| 2537128_SH3YL1 (61) | | | | x | | x | | x |
| 2647124_CPA3 (65) | | x | | x | | x | | x |
| 2647119_CPA3 (69) | 2647109 | x | | x | | x | | x |
| 3554833_CRIP2 (68) | | x | | | | x | 3554818 | |
| 2418590_SLC44A5 (51) | 2418570 | x | 2418570 | x | | | | |
| 2661997_OXTR (43) | 2661992 | | | | 2661992 | x | 2661992 | x |
| 2906733_TREML4 (62) | 2906720 | | | x | | | | |
| 3063538_TRIM4 (52) | 3063536 | x | | x | | x | | |
| 2723770_TBC1D1 (55) | | | | | | | | x |
| 3195045_PTGDS (59) | 3195034 | x | | x | 3195034 | x | | x |
| 2401362_TCEA3 (70) | | | 2401347 | | | | | x |
| 3667896, 97_HPR | 3667890 | | | | | | | |
| 3908171_ZMYND8 | 3908149 | | | | | | | |
| 2545100_HADHA | 2545092 | | | | | | | |

TABLE 10-continued

Comparison of Affymetrix and Nanostring results showed that Affymetrix exon array had higher sensitivity and specificity for prediction.

Genes Included in Each Predictive Model

| Nanostring Probe Set IDs | NC vs SZ/BD Affy ID | Nanostring | NC vs SZ Affy ID | Nanostring | NC vs BD Affy ID | Nanostring | SZ vs BD Affy ID | Nanostring |
|---|---|---|---|---|---|---|---|---|
| 2739191_CCDC109B | 2739160 | | | | | | | |
| 3846545_EEF2 | 3846538 | | | | | | | |
| 3333251, 56, 58, 62, 69, 70, 74_FADS2 | | | | | 3333247 | | 3333247 | |
| 4048243, 52_HLA-DRB5 | | | | | 4048241 | | | |
| 3329128_GYLTL1B | | | 3329099 | | | | | |
| 2660633, 41_IL5RA | | | 2660617 | | | | | |
| 3766938_DDX5 | | | 3766893 | | | | | |
| *AUC | 0.994 | 0.913 | 0.954 | 0.990 | 0.974 | 0.953 | 0.998 | 0.905 |
| Visit 2 Sensitivity | 93.3% | 98.3% | 96.7% | 96.6% | 96.7% | 89.3% | 96.7% | 86.2% |
| Visit 2 Specificity | 100% | 75.0% | 83.3% | 96.4% | 86.7% | 92.9% | 100% | 82.1% |
| Visit 4 Sensitivity | 96.7% | 87.5% | 100% | 75.0% | 93.3% | 75.0% | 96.7% | 57.1% |
| Visit 4 Specificity | 93.3% | 60.0% | 80% | 80.0% | 100.0% | 76.0% | 100% | 85.7% |
| Visit 2 4 Agreement | 93.3% | 77.6% | 86.7% | 76.0% | 88.3% | 75.5% | 100% | 64.2% |

*AUC was for combined visit 2 and 4 modeling and the each visit was evaluated for predictiveness individually Bioinformatics Analysis of Biomarker Panel A recent mega-analysis of differentially expressed genes in SZ across 9 studies was conducted in blood based transcriptomics (Chan et al., Transl Psychiatry 2015; 5: e601). There were 1624 genes that survived FDR that were compared to the top 122 genes identified by ANOVA in the present study. The overlap between studies was not enriched, as 8.7 genes were expected and 9 genes were observed. Interestingly, two mitochondria genes were found in these top 9 and agreed in fold change direction across both studies (Table 11), mitochondrial ribosomal protein L42 (MRPL42), and transcription factor B1, mitochondrial (TFB1M).

TABLE 11

Overlap with mega-analysis of blood dysregulated genes (Chan et al., Transl Psychiatry 2015; 5: e601) and current study.

| Gene Symbol | Gene Product | Mean Difference* | FDR q-Value | Gene Symbol | P-value (SZ vs. NC) | Ratio (SZ vs. NC) |
|---|---|---|---|---|---|---|
| FAM118A | family with sequence similarity 118, member A | −0.37 | 5.90E−04 | FAM118A | 4.17E−13 | 0.58 |
| MRPL42 | mitochondrial ribosomal protein L42 | 0.27 | 1.90E−02 | MRPL42 | 0.000535 | 1.24 |
| PHF14 | PHD finger protein 14 | 0.26 | 2.50E−02 | PHF14 | 3.09E−14 | 0.49 |
| PHIP | pleckstrin homology domain interacting protein | 0.29 | 9.10E−03 | PHIP | 4.66E−29 | 0.59 |
| PLB1 | phospholipase B1 | 0.26 | 3.40E−02 | PLB1 | 2.70E−13 | 1.52 |
| SLC22A4 | solute carrier family 22 (organic cation/zwitterion transporter), member 4 | 0.34 | 3.30E−03 | 5LC22A4 | 0.039619 | 1.14 |
| STX2 | syntaxin 2 | 0.28 | 1.30E−02 | STX2 | 1.49E−05 | 0.81 |
| TFB1M | transcription factor B1, mitochondrial | −0.5 | 3.60E−02 | TFB1M | 1.11E−05 | 0.79 |
| TNFRSF21 | tumor necrosis factor receptor superfamily, member 21 | −0.31 | 3.70E−03 | TNFRSF21 | 1.96E−13 | 0.53 |

Figure 3:
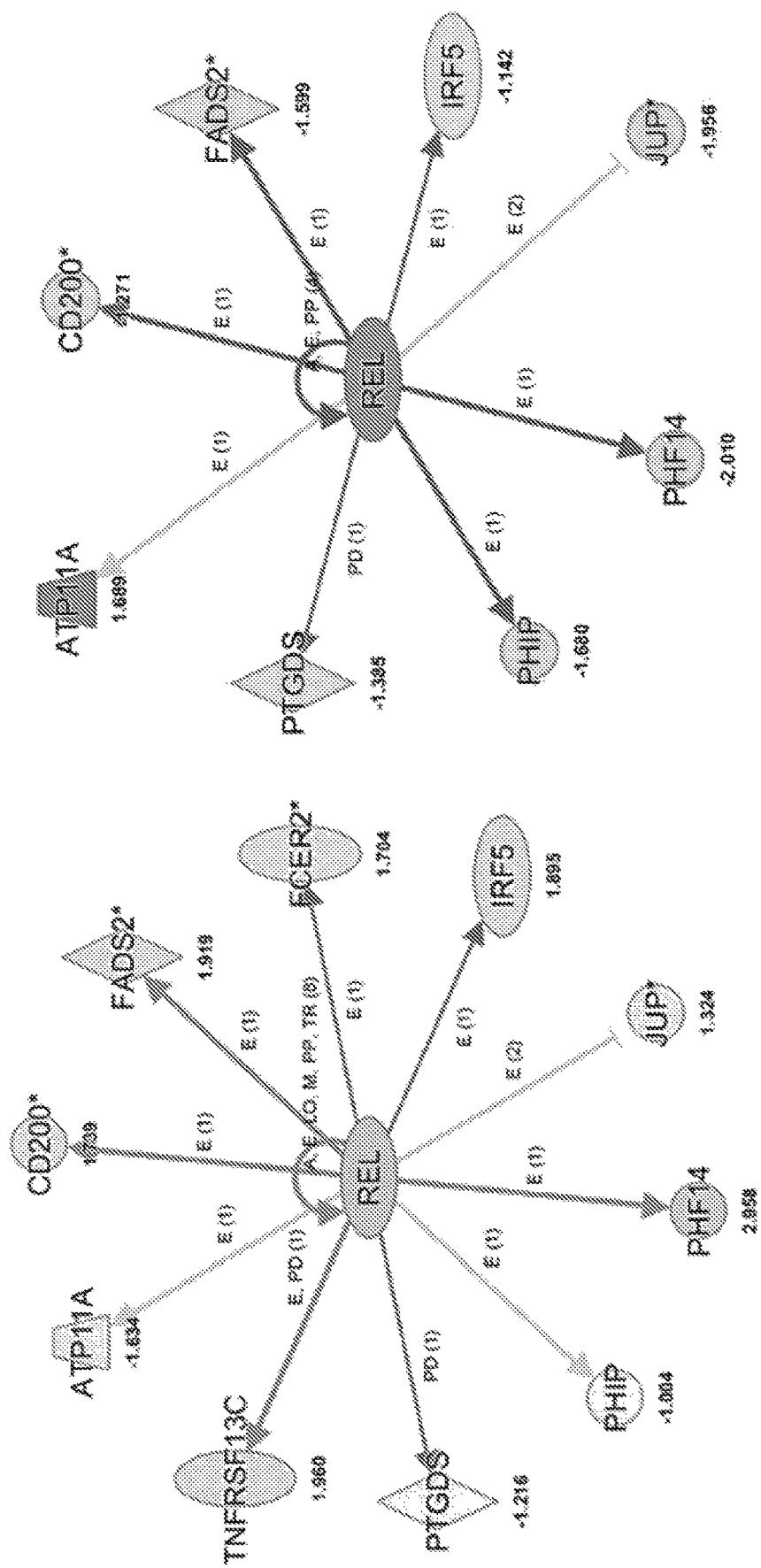
FIG. 3 depicts the results of exemplary experiments demonstrating the REL transcription factor is a central hub for genes in the top 122 differentially expressed list. Left panel shows relationship for BD compared to controls, right panel shows relationship for SZ compared to controls. Many of the genes are oppositely regulated across BD and SZ.

An IPA analysis of the top 122 genes for the BD and SZ biomarker panel showed some overlap in a network related to two different proto-oncogenes, REL and MKL2. The REL gene (REL proto-oncogene, NF-kB subunit) encodes a protein that belongs to the Rel homology domain/immunoglobulin-like fold, plexin, transcription factor (RI-ID/IPT) family. This proto-oncogene plays a role in the survival and proliferation of B lymphocytes. Single nucleotide polymorphisms in this gene are associated with susceptibility to ulcerative colitis and rheumatoid arthritis. The direct REL gene targets were differentially expressed in BD and SZ (FIG. 3).

As examples, the opposite fold change genes related to REL were seen in BD and SZ, ATP11A was upregulated in SZ (1.68) and down-regulated in BL) (−1.63), while an opposite relationship was seen for PHF14 downregulated in SZ (−2.01) and upregulated in BD (2.95).

Figure 4:
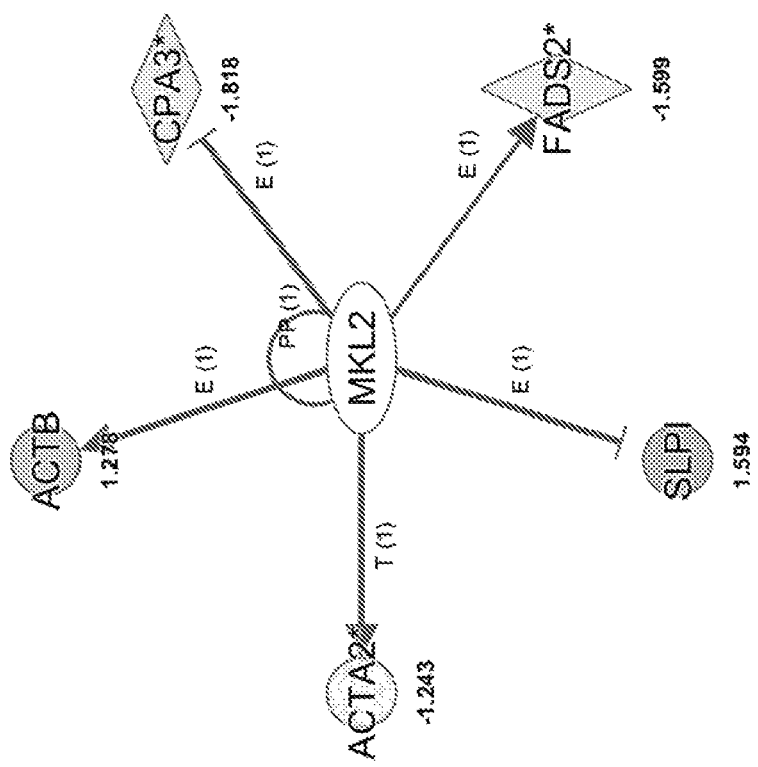
FIG. 4 depicts the results of exemplary experiments demonstrating the MKL2 proto-oncogene is a central hub for genes in the top 122 differentially expressed list. Left panel shows relationship for BD compared to controls, right panel shows relationship for SZ compared to controls. Many of the genes are oppositely regulated across BD and SZ.
Figure 4:
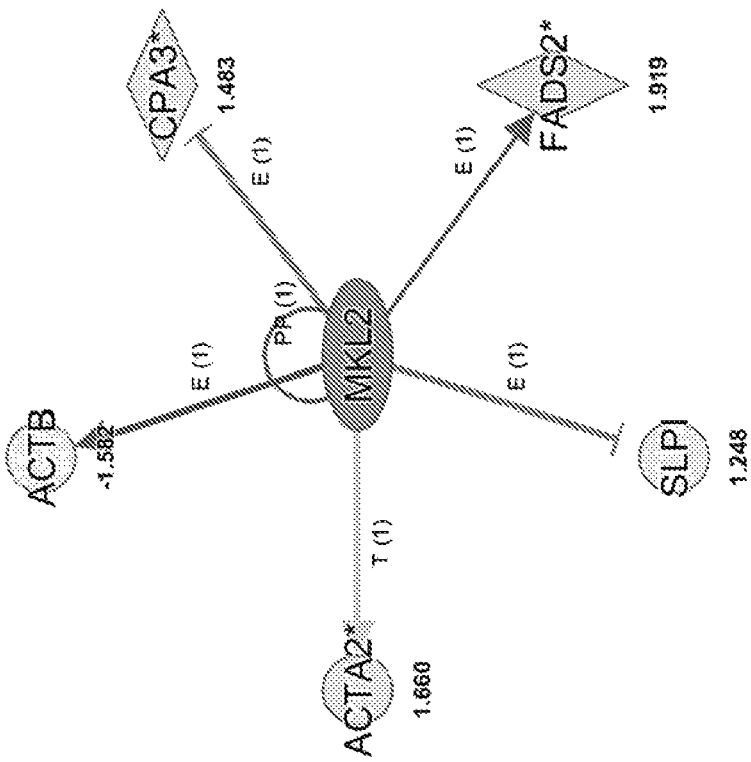

MKL2 is a proto-oncogene, which is widely distributed, highly expressed in brain regions such as dentate gyrus (Allen Institute Brain Science (Hawrylycz et al., Nature 2012; 489(7416): 391-399)) and associated with microcephaly (Ramos et al., (Clin Genet 2014; 85(5): 423-432). The MKL2 gene consists of multiple exons, many of those exons are down-regulated in SZ and not changed significantly in BD. The exon levels in blood for MKL2 were significantly differentially expressed in SZ, although not in the top 300 genes (FIG. 4). The downstream effects on MKL2 regulated genes in the top biomarker classification genes were in the expected directions, e.g. there were decreased fold changes seen in genes regulated by MKL2 in SZ (ACTA2, FADS2, CPA3), while the same set was up-regulated in BD.

Two additional genes in the biomarker panels PTGDS (prostaglandin D2 synthase) and FADS2 (fatty acid desaturase 2) were also found to be candidate genes in the literature. PTGDS expression was reduced in BD PBMC (Munkholm et al., Int J Neuropsychopharmacol 2014; 18(5): pyu101), and also in the present study (p=fold change −1.23) and also down in SZ (p==9.04E-12, fold change −1.52). In BD and SZ there appears to be a down regulation of PTGDS, which also was ranked high in the convergent functional genomics paradigm for anxiety (Le-Niculescu et al., Transl Psychiatry 2011; 1: e9).

FADS2 expression was decreased in schizophrenia in this study (p-value 9.20E-09, fold change −1.80) and increased in BD (p-value 2.79E-06, fold change=1.6). The FADS2 and PTGDS genes work in the biosynthesis of fatty acids pathway, and converge on key molecules in BD such as arachidonic acid. HADHA was significantly increased in BD (p=4.74E-08, fold change 1.67) and was not changed in SZ. HADHA is closely related in the fatty acid pathway with FADS2 and HADHA along with PTGDS participating in biosynthesis and degradation of unsaturated fatty acids, an important pathway implicated in BD and SZ.

Example 2: BD-SZ-NC Comparison

These results demonstrate the identification of a gene panel to discriminate bipolar and schizophrenic subjects from normal controls from 122 top known genes. Forward stepwise variable selection with logistic regression modeling was used to identify a set of genes which would significantly differentiate the combined bipolar and schizophrenic subjects from the normal controls.

Table 12 includes the set of 11 genes that are diagnostic for this purpose.

TABLE 12

| Marker | Transcript ID | Gene |
|---|---|---|
| 77 | 3667890 | HPR |
| 5 | 2906720 | TREML4 |
| 52 | 3908149 | ZMYND8 |
| 36 | 3195034 | PTGDS |
| 100 | 2647109 | CPA3 |
| 82 | 3063536 | TRIM4 |
| 41 | 2418570 | SLC44A5 |
| 97 | 2661992 | OXTR |
| 43 | 2545092 | HADHA |
| 59 | 2739160 | CCDC109B |
| 117 | 3846538 | EEF2 |

Table 13 includes the model fit for visits 2 and 4.

TABLE 13

Visits 2 and 4
AIC Intercept only 231.145
AIC with genes 57.157

| | Estimate | P-value |
|---|---|---|
| intercept $\beta_0$ | −66.4124 | 0.0048 |
| marker 77 coefficient $\beta_1$ | −5.2531 | 0.0001 |
| marker 5 coefficient $\beta_2$ | 2.0403 | 0.0008 |
| marker 52 coefficient $\beta_3$ | −3.0311 | 0.0010 |
| marker 36 coefficient $\beta_4$ | 8.9782 | 0.0003 |
| marker 100 coefficient $\beta_5$ | 4.9250 | 0.0008 |
| marker 82 coefficient $\beta_6$ | −2.4530 | 0.0032 |
| marker 41 coefficient $\beta_7$ | 3.1667 | 0.0020 |
| marker 97 coefficient $\beta_8$ | 2.3342 | 0.0030 |
| marker 43 coefficient $\beta_9$ | 2.3378 | 0.0007 |
| marker 59 coefficient $\beta_{10}$ | 1.9140 | 0.0016 |
| marker 117 coefficient $\beta_{11}$ | −7.0097 | 0.0019 |
| ROC AUC | 0.995 | <0.0001 |

Prob of Normal Control from Logistic =

$$\frac{1}{1 + \exp[-(\beta_0 + \beta_1 M77 + \beta_2 M5 + \beta_3 M52 + \beta_4 M36 + \beta_5 M100 + \beta_6 M82 + \beta_7 M41 + \beta_8 M97 + \beta_9 M43 + \beta_{10} M59 + \beta_{11} M117)]}$$

Figure 6:
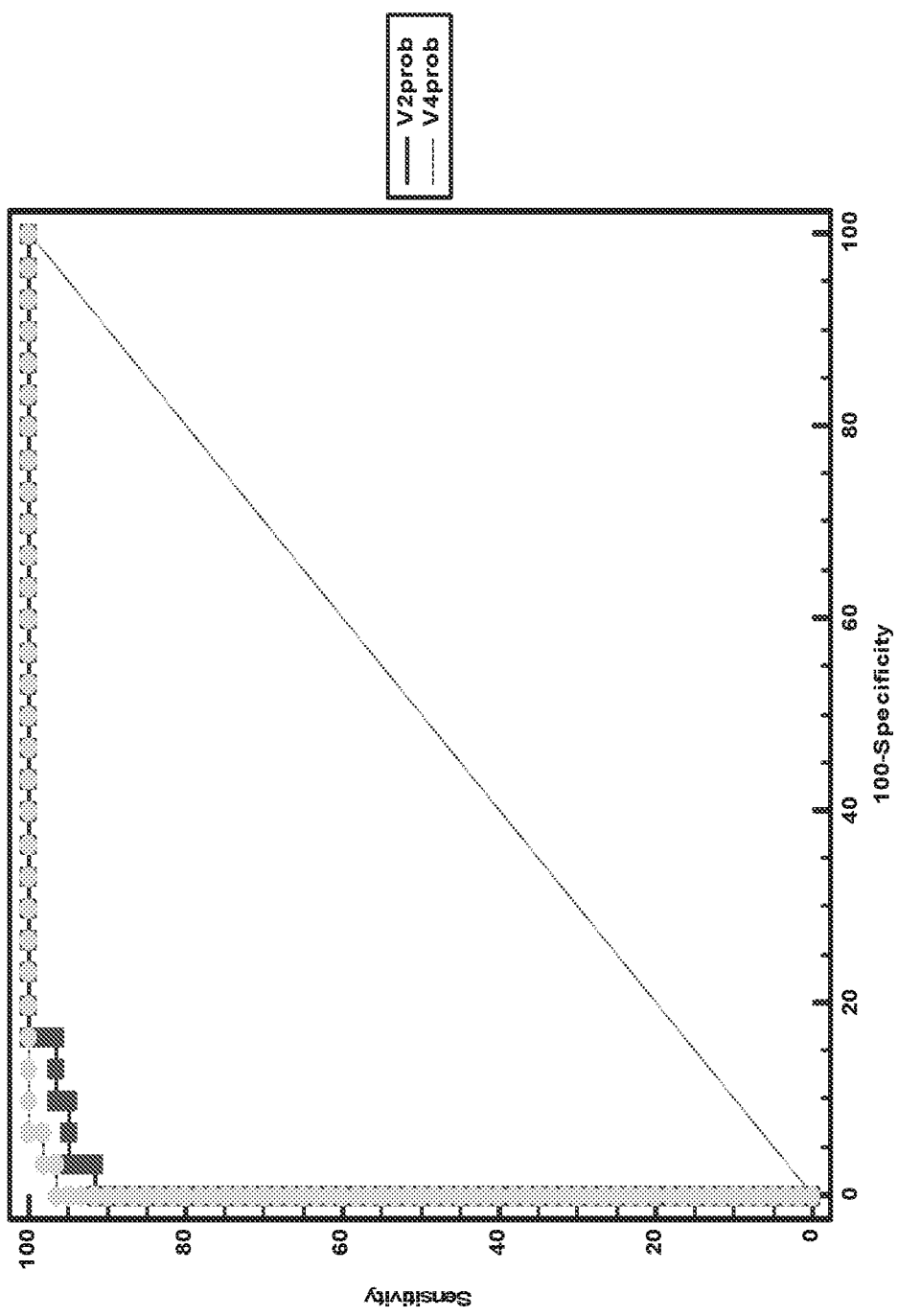
FIG. 6 is a graph of experimental data demonstrating logistic model estimated probabilities for visits 2 and 4.

Optimal cut-point for discriminating two populations is Schiz or Bipolar if Prob(NC) from Logistic ≤0.1518
At this cut-point, across both visits
Sensitivity=93.33 (95% CI 87.3–97.1)
Specificity=100.00 (95% CI 94.0–100)
FIG. 6 shows the ROC curve for visits 2 and 4.
Table 14 includes data using the 0.1518 cut-point for a positive test.

TABLE 14

| | Visit 2 | | Visit 4 | |
|---|---|---|---|---|
| Gene Model | NC | BD/SZ | NC | BD/SZ |
| ≤0.1518 | 0 | 28/26 | 0 | 29/29 |
| >0.1518 | 30 | 2/4 | 30 | 1/1 |

Figure 7:
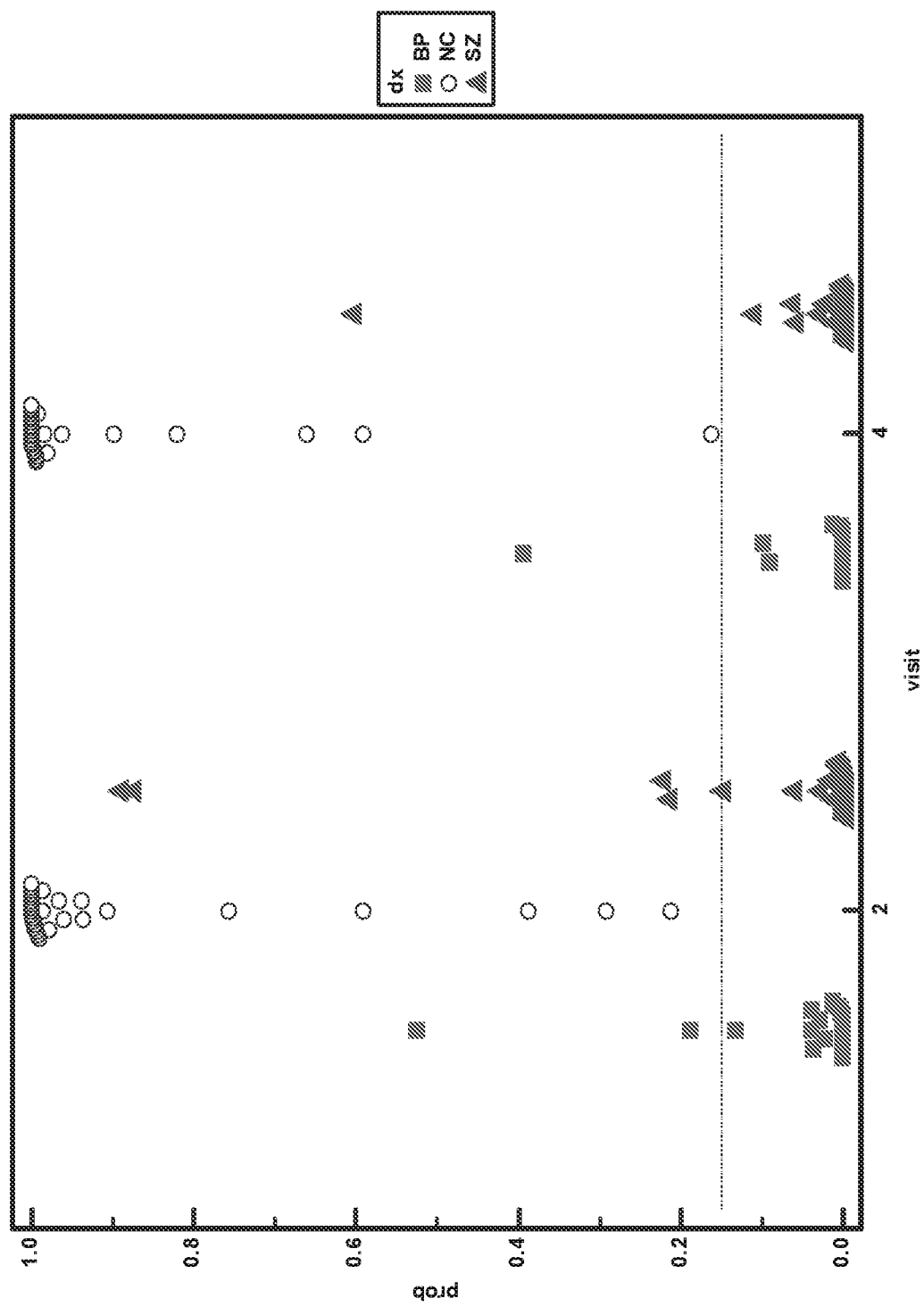
FIG. 7 is a graph of experimental data demonstrating the logistic model estimated probabilities for each group, for each visit along with the reference line for the 0.1518 cut-point.

FIG. 7 shows the logistic model estimated probabilities for each group, for each visit along with the reference line for the 0.1518 cut-point. The visit 2 probabilities are significantly correlated with the visit 4 probabilities (p<0.0001) with r=0.89 (95% CI 0.83-0.92).

Table 15 includes data demonstrating that 93% of the subjects (84/90) received the same diagnostic outcome from visit 2 to visit 4.

TABLE 15

|  |  | Visit 4 | |
|---|---|---|---|
| | | ≤0.1518 | >0.1518 |
| All | Visit 2 | | |
| | <0.1518 | 53 | 1 |
| | >0.1518 | 5 | 31 |
| NC | Visit 2 | ≤0.1518 | >0.1518 |
| | ≤0.1518 | | |
| | >0.1518 | | 30 |
| BD | Visit 2 | ≤0.1518 | >0.1518 |
| | ≤0.1518 | 27 | 1 |
| | >0.1518 | 2 | |
| SZ | Visit 2 | ≤0.1518 | >0.1518 |
| | ≤0.1518 | 26 | |
| | >0.1518 | 3 | 1 |

Example 3: BD-NC Comparison

These results demonstrate the identification of a gene panel to discriminate bipolar subjects from normal controls from 122 top known genes. Forward stepwise variable selection with logistic regression modeling was used to identify a set of genes which would significantly differentiate the bipolar subjects from the normal controls.

The set of 4 genes that may be diagnostic for this purpose are listed in Table 16.

TABLE 16

| Marker | Transcript ID | Gene |
|---|---|---|
| 97 | 2661992 | OXTR |
| 76 | 4048241 | HLA-DRB5 |
| 50 | 3333247 | FADS2 |
| 36 | 3195034 | PTGDS |

Table 17 includes the model fit for visits 2 and 4.

TABLE 17

| Visits 2 and 4 | | |
|---|---|---|
| AIC Intercept only | 168.355 | |
| AIC with genes | 45.986 | |
| | Estimate | P-value |
| intercept $\beta_0$ | −39.9111 | 0.0006 |
| marker 97 coefficient $\beta_1$ | 5.4440 | <0.0001 |
| marker 76 coefficient $\beta_2$ | −0.6870 | 0.0012 |
| marker 50 coefficient $\beta_3$ | −3.7201 | 0.0010 |
| marker 36 coefficient $\beta_4$ | 3.5108 | 0.0026 |
| ROC AUC | 0.987 | <0.0001 |

$$\text{Prob of Normal from Logistic} = \frac{1}{1+\exp[-(\beta_0+\beta_1 M97+\beta_2 M76+\beta_3 M50+\beta_4 M36)]}$$

Optimal cut-point for discriminating two populations is BD if Prob(NC) from Logistic ≤0.659

At this cut-point, across both visits

Sensitivity=98.33 (95% CI 91.1-100)

Specificity=90.00 (95% CI 79.5-96.2)

Figure 5:
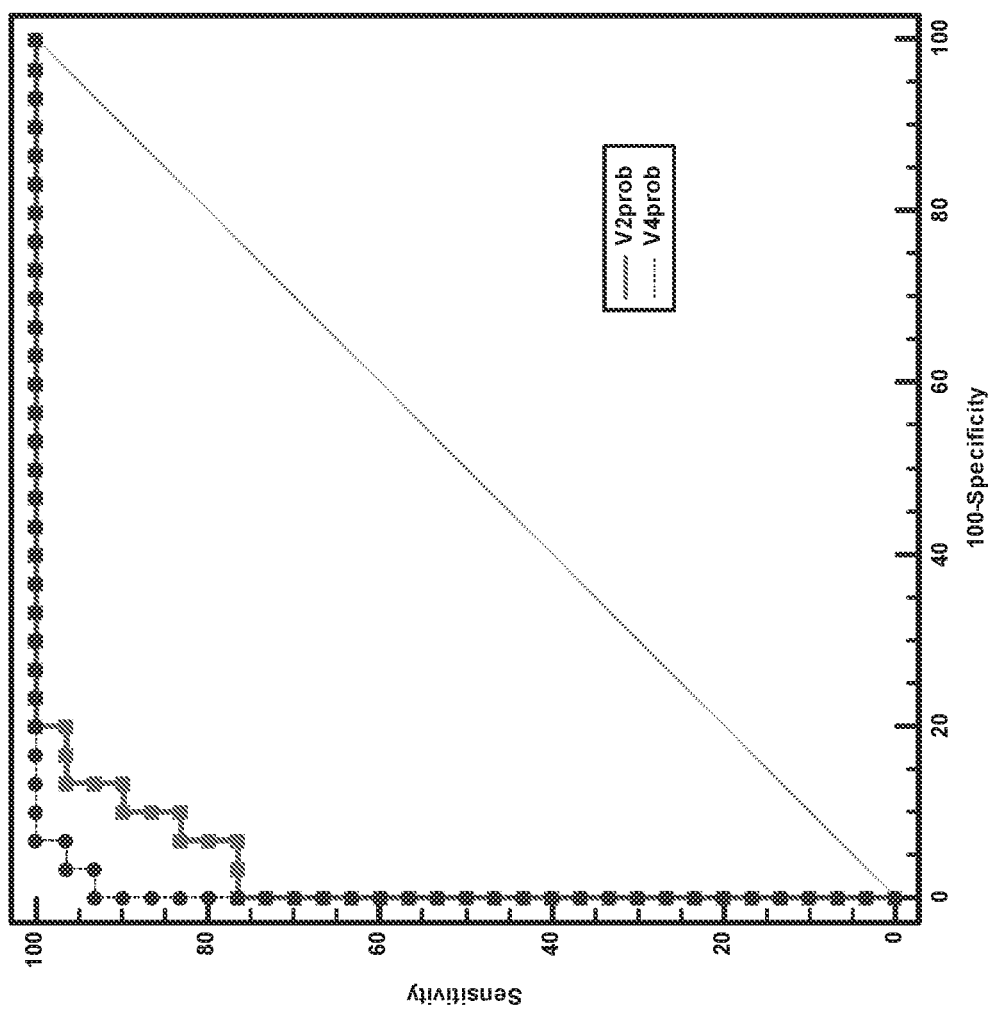
FIG. 5 is a graph of experimental data demonstrating the ROC curve for visits 2 and 4.

The ROC Curve for visits 2 and 4 is shown in FIG. 5.

Table 18 shows the data using the 0.659 cut-point for a positive test.

TABLE 18

| | Visit 2 | | Visit 4 | |
|---|---|---|---|---|
| Gene Model | NC | BD | NC | BD |
| ≤0.659 | 4 | 29 | 2 | 30 |
| >0.659 | 26 | 1 | 28 | 0 |

Visit specific metrics:

| Sensitivity | 0.97 | 1.00 |
|---|---|---|
| Specificity | 0.87 | 0.93 |
| Accuracy | 0.92 | 0.97 |

Figure 8:
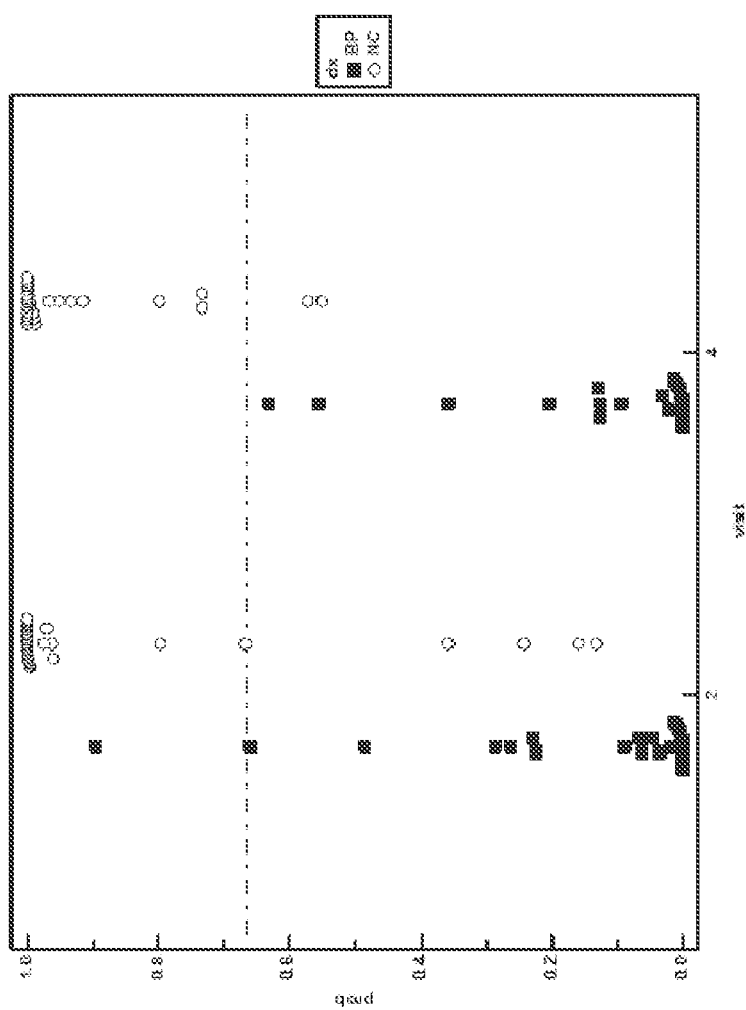
FIG. 8 is a graph of experimental data demonstrating logistic model estimated probabilities for visits 2 and 4.

FIG. 8 shows the logistic model estimated probabilities for each group, for each visit along with the reference line for the 0.659 cut-point. The visit 2 probabilities are significantly correlated with the visit 4 probabilities (p<0.0001) with r=0.86 (95% CI 0.78-0.92).

92% of the subjects (55/60) received the same diagnostic outcome from visit 2 to visit 4 (Table 19).

TABLE 19

| | Visit 4 | |
|---|---|---|
| Visit 2 | ≤0.659 | >0.659 |
| ≤0.659 | 30 | 3 |
| >0.659 | 2 | 25 |

Example 4: BD-SZ Comparison

These results demonstrate the identification of a gene panel to discriminate bipolar subjects from schizophrenic subjects from 122 top known genes. Forward stepwise variable selection with logistic regression modeling was used to identify a set of genes which would significantly differentiate the bipolar subjects from the schizophrenic subjects.

The set of 3 genes that may be diagnostic for this purpose are listed in Table 20. Markers 97 and 50 were also identified in the BD-NC panel.

TABLE 20

| Marker | Transcript ID | Gene |
|---|---|---|
| 37 | 3554818 | CRIP2 |
| 97 | 2661992 | OXTR |
| 50 | 3333247 | FADS2 |

Table 21 includes the model fit for visits 2 and 4.

TABLE 21

| Visits 2 and 4 | | |
|---|---|---|
| AIC Intercept only 168.355 | | |
| AIC with genes 24.662 | | |
| | Estimate | P-value |
| intercept $\beta_0$ | −28.7571 | 0.0403 |
| marker 37 coefficient $\beta_1$ | 7.3345 | 0.0123 |
| marker 97 coefficient $\beta_2$ | −8.5153 | 0.0054 |
| marker 50 coefficient $\beta_3$ | 4.1472 | 0.0044 |
| ROC AUC | 0.996 | <0.0001 |

$$\text{Prob of Bipolar from Logistic} = \frac{1}{1 + \exp[-(\beta_0 + \beta_1 M37 + \beta_2 M97 + \beta_3 M50)]}$$

Optimal cut-point for discriminating two populations is Schiz if Prob(BD) from Logistic ≤0.2857

At this cut-point, across both visits

Sensitivity=96.67 (95% CI 88.5-99.6)

Specificity=100 (95% CI 94-100)

Figure 9:
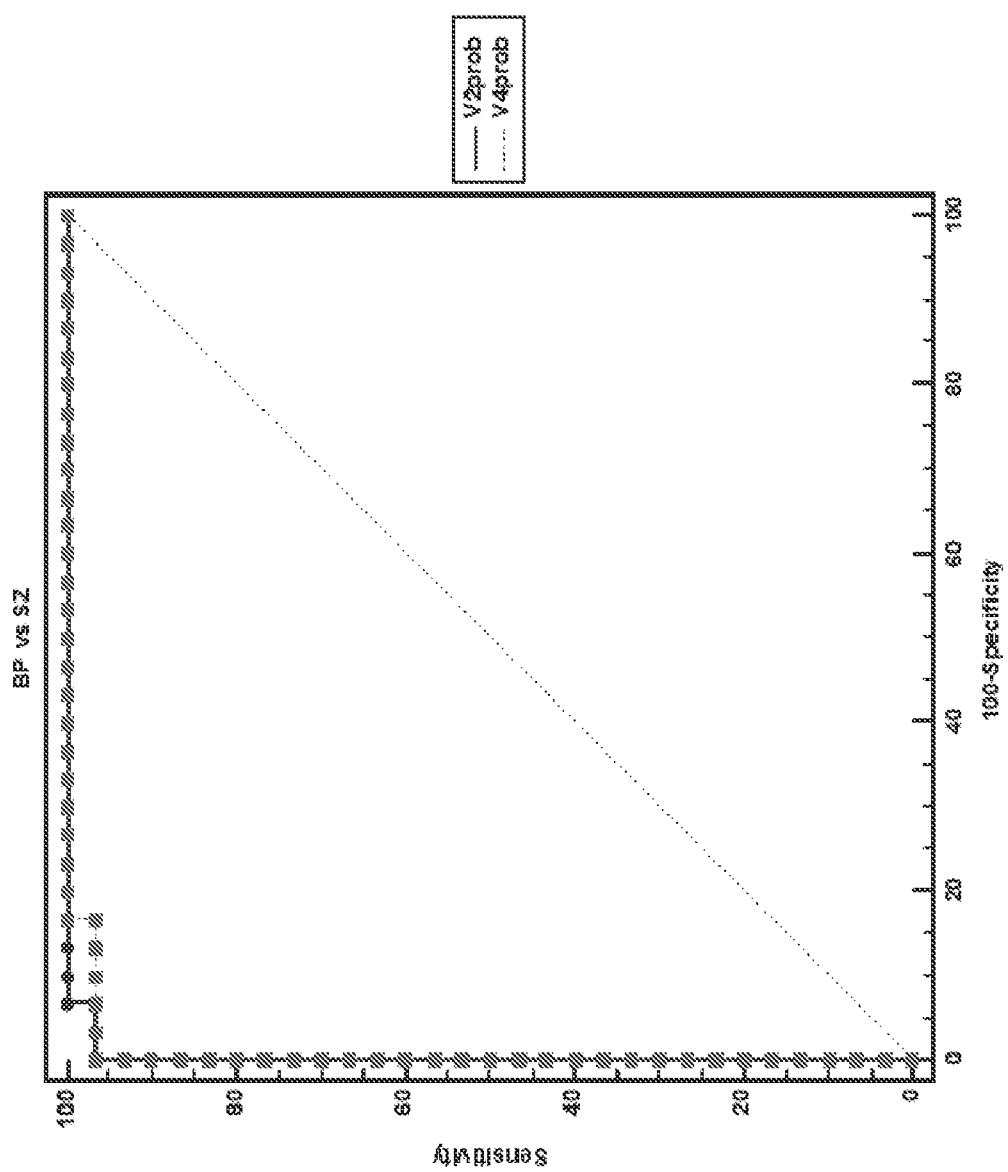
FIG. 9 is a graph of experimental data demonstrating the ROC curve for visits 2 and 4 for BD vs SZ.

FIG. 9 includes the ROC curve for visits 2 and 4.

Table 22 includes data for using the 0.2857 cut-point for a positive SZ test.

TABLE 22

| Gene Model | Visit 2 | | Visit 4 | |
|---|---|---|---|---|
| | BD | SZ | BD | SZ |
| ≤0.2857 | 0 | 29 | 0 | 29 |
| >0.2857 | 30 | 1 | 30 | 1 |

Visit specific metrics: Visit 2 Visit 4

| | | |
|---|---|---|
| Sensitivity (SZ) | 0.97 | 0.97 |
| Specificity (BD) | 100 | 100 |
| Accuracy | 0.98 | 0.98 |

Figure 10:
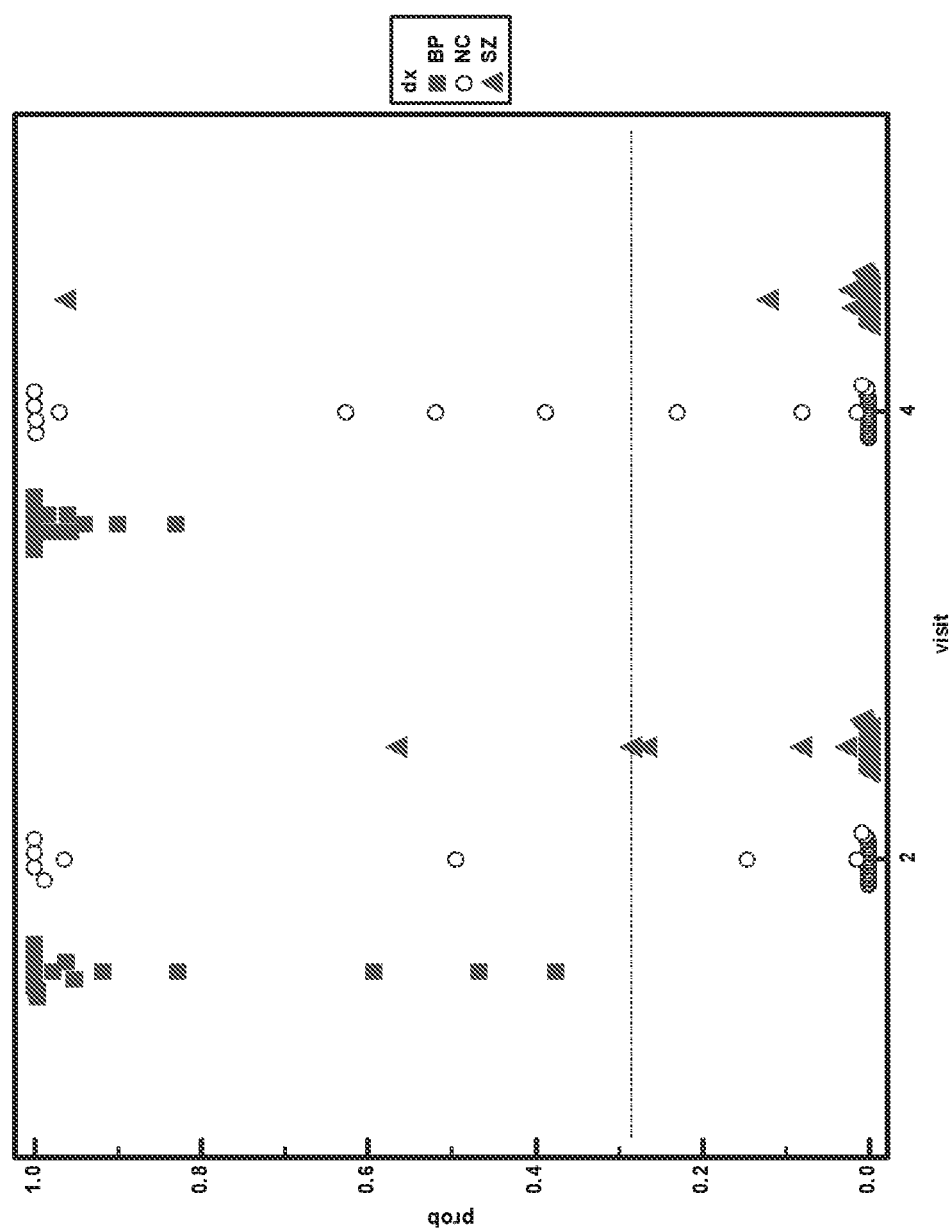
FIG. 10 is a graph of experimental data demonstrating the logistic model estimated probabilities for each group.

FIG. 10 shows the logistic model estimated probabilities for each group, for each visit along with the reference line for the 0.2857 cut-point. The NC subjects are added in using the predictive model for the BD vs SZ. The visit 2 probabilities are significantly correlated with the visit 4 probabilities (p<0,0001) with r-0.96 (95% CI 0.94-0.98).

Table 23 includes data demonstrating that 100% of the subjects (60/60) received the same diagnostic outcome from visit 2 to visit 4.

TABLE 23

| | Visit 4 | |
|---|---|---|
| Visit 2 | ≤0.2857 | >0.2857 |
| ≤0.2857 | 29 | 0 |
| >0.2857 | 0 | 31 |

Leave One Out Cross Validation

Each subject was sequentially removed, the logistic model was fit with the remaining 59 subjects and the model fit to predict the subject who was left out was used. (Table 24). The leave-one-out model used for this analysis has higher accuracy because the model was based upon combined Visit 2 and Visit 4 data, then run on each individual visit.

TABLE 24

| | V2 Actual | | V4 Actual | | Both Actual | |
|---|---|---|---|---|---|---|
| Predicted | BD | SZ | BD | SZ | BD | SZ |
| BD | 27 | 1 | 30 | 1 | 57 | 2 |
| SZ | 3 | 29 | 0 | 29 | 3 | 58 |
| | Accuracy 93% | | Accuracy 98% | | Accuracy 96% | |
| | Sensitivity (SZ) 97% | | Sensitivity (SZ) 97% | | Sensitivity (SZ) 97% | |
| | Specificity (BD) 90% | | Specificity (BD) 100% | | Specificity (BD) 95% | |

Example 5: Analyses of Un-Normalized Gene Expression Data

TABLE 25

(BD + SZ) vs. NC Comparison (visits 2 and 4)

| Parameter | Estimate | Std Err | P-value |
|---|---|---|---|
| Intercept | 44.9621 | 10.2406 | <.0001 |
| TREML4 | −0.6979 | 0.2658 | 0.0087 |
| PTGDS | −4.3427 | 0.9990 | <.0001 |
| SLC44A5 | −1.9189 | 0.4810 | <.0001 |
| HADHA | −0.9526 | 0.3386 | 0.0049 |
| ZMYND8 | 0.8177 | 0.3431 | 0.0171 |
| GYLTL1B | 3.2553 | 0.7704 | <.0001 |
| CCDC109B | −1.0542 | 0.2868 | 0.0002 |
| HPR | 2.5108 | 0.5648 | <.0001 |
| TRIM4 | 2.1397 | 0.5594 | 0.0001 |
| OXTR | −2.5848 | 0.6609 | <.0001 |
| CPA3 | −1.1792 | 0.4616 | 0.0106 |

ROC AUC 0.973
P(model) = 0.0005

TABLE 26

BD vs. NC Comparison (visits 2 and 4)

| Parameter | Estimate | Std Err | P-value |
|---|---|---|---|
| Intercept | 39.6860 | 9.1607 | <.0001 |
| OXTR | −2.7173 | 0.6667 | <.0001 |
| PTGDS | −3.2692 | 0.8294 | <.0001 |
| TREML4 | −0.6789 | 0.2640 | 0.0101 |
| SLC44A5 | −1.9348 | 0.4797 | <.0001 |
| GYLTL1B | 1.3459 | 0.6449 | 0.0369 |
| HPR | 1.4963 | 0.4466 | 0.0008 |
| TRIM4 | 1.6745 | 0.4938 | 0.0007 |

ROC AUC 0.951
P(model) = 0.0007

TABLE 27

SZ vs. NC Comparison (visits 2 and 4)

| Parameter | Estimate | Std Err | P-value |
|---|---|---|---|
| Intercept | −13.4445 | 6.7739 | 0.0472 |
| TREML4 | 0.5711 | 0.2415 | 0.0181 |
| PTGDS | 3.1815 | 0.9906 | 0.0013 |
| SLC44A5 | 1.7258 | 0.5215 | 0.0009 |
| GYLTL1B | −3.1913 | 0.9423 | 0.0007 |
| HPR | −1.7817 | 0.4715 | 0.0002 |
| TRIM4 | −1.3580 | 0.4218 | 0.0013 |
| CPA3 | 1.8422 | 0.5090 | 0.0003 |

ROC AUC 0.952
P(model) = 0.0003

TABLE 28

SZ vs. BD Comparison (visits 2 and 4)

| Parameter | Estimate | Std Err | P-value |
|---|---|---|---|
| PTGDS | 2.5861 | 0.7034 | 0.0002 |
| SLC44A5 | 1.9851 | 0.5742 | 0.0005 |
| GYLTL1B | −3.5039 | 0.9396 | 0.0002 |
| HPR | −2.2558 | 0.5812 | 0.0001 |
| TRIM4 | −1.9102 | 0.4765 | <.0001 |
| CPA3 | 1.5558 | 0.4348 | 0.0003 |
| CCDC109B | 0.8509 | 0.2720 | 0.0018 |

ROC AUC 0.961
P(model) = 0.0006

TABLE 29

Old and New Model Fit Comparison

| | New Un-normalized Gene Expression | | | | Old Normalized Gene Expression | | | |
|---|---|---|---|---|---|---|---|---|
| | BDSZ vs NC | SZ vs NC | BD vs NC | BD vs SZ | BDSZ vs NC | SZ vs NC | BD vs NC | BD vs SZ |
| HPR | X | X | X | X | X | | | |
| TREML4 | X | X | X | | X | | | |
| ZMYND8 | X | | | | X | | | |
| PTGDS | X | X | X | X | X | | X | |
| CPA3 | X | X | | X | X | | | |
| TRIM4 | X | X | X | X | X | | | |
| SLC44A5 | X | X | X | X | X | X | | |
| OXTR | X | | X | | X | | X | X |
| HADHA | X | | | | X | | | |
| CCDC109B | X | | | X | X | | | |
| GYLTL1B | X | X | X | X | | X | | |
| EEF2 | | | | | X | | | |
| TCEA3 | | | | | | X | | |
| CRIP2 | | | | | | | | X |
| FADS2 | | | | | | | X | X |
| IL5RA | | | | | | X | | |
| HLA_DRB5 | | | | | | | X | |
| DDX5 | | | | | | X | | |
| AUC | 0.973 | 0.952 | 0.951 | 0.961 | 0.995 | 0.967 | 0.987 | 0.996 |
| P(Model) | 0.0005 | 0.0003 | 0.0007 | 0.0006 | <0.0001 | <0.0001 | <0.0001 | <0.0001 |

Example 6: Analysis of Illumina Data for Neuroleptic-Free Subjects and Other Analyses Table 30 includes data of Illumina SZ genes, logistic regression fit to data, subgrouped by age <30 and/or neuroleptic-free status.

SZ genes: TREML4, PTGDS, SLC44A5, GYLTL1B, HPR, TRIM4, CPA3

Second HPR probe was used because first has missing data. First TRIM4 probe was used as it fit better than second AUC.

TABLE 30

| Subjects | NC N | SZ N | ROC Illumina SZ genes, logistic regression fit to data, | Sensitivity | Specificity | Cutpoint |
|---|---|---|---|---|---|---|
| All Illumina Subjects | 118 | 121 | 0.686 | 84.3% | 36.4% | 0.423 |
| Illumina Subjects with Age <30 | 44 | 31 | 0.782 | 58.1% | 90.9% | 0.551 |

TABLE 30-continued

| Subjects | NC N | SZ N | ROC Illumina SZ genes, logistic regression fit to data, | Sensitivity | Specificity | Cutpoint |
|---|---|---|---|---|---|---|
| Neuroleptic-free Illumina Subjects | 22 | 15 | 0.642 | 80.0% | 59.1% | 0.364 |
| Neuroleptic-free, Age <30 Subjects | 14 | 8 | 0.866 | 100.0% | 71.4% | 0.308 |

Table 31 includes data from the first "All Illumina Subjects" analysis, the predicted classification of the neuroleptic-free subjects.

TABLE 31

|  | Actual SZ N = 15 | Actual NC N = 22 |
|---|---|---|
| Predicted NC | 8 | 18 |
| Predicted SZ | 7 | 4 |
|  | Sensitivity = 46.7% | Specificity = 81.8% |

Logistic Model with 7 SZ genes, age indicator (<30, ≥30), neuroleptic-free (Y,N)
  ROC AUC=0.702 Sensitivity=64.5% Specificity=69.5%
  Significance of age indicator term in model p=0.1163
  Significance of neuroleptic-free term in model p=0.0362

7 SZ genes from "New" panel were compared with all 10* genes from "New" panel vs. 17* genes from "Old" panel (Table 32).

7 SZ genes from New panel: TREML4, PTGDS, SLC44A5, GYLTL1B, HPR, TRIM4, CPA3

Additional 3 genes from New panel: ZMYND8, OXTR, HADHA

Additional 7 genes from Old panel: EEF2, TCEA3, CRIP2, FADS2, IL5RA (2 different probes included), HLA-DRB5, DDX5

*CCDC109B which was included on both new and old panels is not available on Illumina dataset Note: used second HPR probe as first has missing data, used first TRIM4 probe as better fitting than second.

TABLE 32

| Subjects | Gene Set | NC N | SZ N | ROC AUC | Sensitivity | Specificity | Cutpoint |
|---|---|---|---|---|---|---|---|
| All Subjects | 7 SZ from New | 118 | 121 | 0.686 | 84.3% | 36.4% | 0.423 |
| All Subjects | All 10 from New | 118 | 121 | 0.695 | 81.8% | 30.5% | 0.406 |
| All Subjects | All 17 from Old | 118 | 121 | 0.731 | 59.5% | 80.5% | 0.574 |
| NL Free Subj | 7 SZ from New | 22 | 15 |  | 46.7% | 81.8% |  |
| NL Free Subj | All 10 from New | 22 | 15 |  | 46.7% | 72.7% |  |
| NL Free Subj | All 17 from Old | 22 | 15 |  | 20.0% | 81.8% |  |

Example 7: Comparison of SZ Genes from 11-Gene Panel vs 18-Gene Panel in Original Median-Normalized Affymetrix Exon Array Data and Performance in Gender, Age Subgroups SZ genes From 18 gene panel: SLC44A5, GYLTL1B, TCEA3, IL5RA, DDX5

From 11-gene panel: HPR, TREML4, PTGDS, CPA3, TRIM4, SLC44A5

TABLE 33

Comparison of SZ genes from 11-gene panel vs 18-gene panel

| Panel | Group (visits 2 and 4 combined) | NC N | SZ N | ROC AUC | Sensitivity | Specificity | Cut-point |
|---|---|---|---|---|---|---|---|
| 18-gene | All subjects | 60 | 60 | 0.967 | 90.0% | 88.3% | 0.499 |
| | Male, <30 yrs | 16 | 10 | 0.913 | 90.0% | 81.3% | 0.572 |
| | Male, ≥30 yrs | 28 | 34 | 0.993 | 97.1% | 100.0% | 0.411 |
| | Female | 16 | 16 | 0.996 | 100.0% | 93.8% | 0.659 |
| 11-gene | All subjects | 60 | 60 | 0.975 | 93.3% | 90.0% | 0.549 |
| | Male, <30 yrs | 16 | 10 | 0.944 | 90.0% | 81.3% | 0.774 |
| | Male, ≥30 yrs | 28 | 34 | 0.989 | 97.1% | 89.3% | 0.574 |
| | Female (only HPR and CPA3) | 16 | 16 | 0.926 | 100.0% | 75.0% | 0.694 |

A better diagnostic was not observed in young males as seen in Illumina data (not enough females to split by age)

The two panels were very close, with slightly better diagnostic in all subjects with 11-gene panel.

Example 8: Independent Study of Biomarker Signature Validation

The de Jong et al., 2012 (de Jong et al., PLoS One 2012; 7(6): e39498) results provide an independent validation of the SZ signature, with a high ROC shown in subjects with schizophrenia <30 years of age and in antipsychotic-free subjects with schizophrenia <30 years of age. These results suggest that the signature can be analyzed in young patients that are medication free at the time of testing as well as patients being treated with antipsychotic medications at the time of testing.

The Materials and Methods are Now Described

The initial whole blood exon array signature from Example 1 was tested against an independent dataset referred to in deJong et al., 2012 (de Jong et al., PLoS One 2012; 7(6): e39498) and made available under GEO dataset omnibus accession GSE38485.

deJong et al. applied a systems biology approach to genome-wide expression data from whole blood of 92 medicated and 29 antipsychotic-free schizophrenia patients and 118 healthy controls. They showed that gene expression profiling in whole blood can identify twelve large gene co-expression modules associated with schizophrenia.

The Results are Now Described

The three datasets described in Table 33 reported by deJong et al., 2012 (de Jong et al., PLoS One 2012; 7(6): e39498) were independently reanalyzed for the studies presented herein. Dataset 1 includes schizophrenia patients on antipsychotics (n=92) and healthy controls (n=78). Dataset 2 consists of n=29 antipsychotic-free schizophrenia patients and n=40 healthy controls. The demographic information for both datasets is given in Table 34.

TABLE 34

Description of datasets from de Jong et al., 2012 (de Jong et al., PLoS One 2012; 7(6): e39498).

| | Schizophrenia dataset | | Antipsychotic-free dataset | |
|---|---|---|---|---|
| | Controls | Cases | Controls | Cases |
| Total | 78 | 92 | 40 | 29 |
| Mean age | 41 yrs | 41 yrs | 30 yrs | 31 yrs |
| Gender | 31M, 47F | 66M, 26F | 27M, 13F | 21M, 8F |
| Batch 1 | | | 22 | 15 |
| Batch 2 | 78 | 92 | 18 | 14 |
| Country* | 22 DK, 56 NL | 92 NL | 6 DK, 34 NL | 6 DK, 23 NL |
| Expression Array | Illumina H-12 (16,707 genes) | | Illumina H-8 & H-12 (12,704 genes) | |

Two datasets are shown, schizophrenia cases and controls, and antipsychotic-free schizophrenia and control dataset. Age and gender information is given for cases and controls separately for antipsychotic free subjects in Table 34. Gene expression data was generated in two batches (batch 1: Illumina H-8 and batch 2: Illumina H-12) and collected at different sites, information given in the fourth and fifth row). The number of expressed genes is given in the last row.
*DK=Denmark and ML=The Netherlands.

Subjects in de Jong et al., 2012

Participants were recruited from three sources: i) the Department of Psychiatry of the University Medical Center Utrecht (90 controls and 113 cases), ii) Parnassia Psycho-Medical Center in the The Netherlands (2 cases) and iii) the Center for Neuropsychiatric Schizophrenia Research, Psychiatric Center Glostnip, Denmark (28 controls and 6 cases). Diagnoses were determined by Standardized Psychiatric interviews either The Comprehensive Assessment of Symptoms and History (CASH) or the Composite international diagnostic interview (CIDI) by trained clinicians. Schizophrenia was defined by a DSM-IV-TR diagnosis of #295.0-295.89, and #298.9.

Antipsychotic-free patients were not on antipsychotics during the six-month-period prior to blood sampling, Only cases with a DSM IV #295.0-295.89 and #298.9 diagnoses were included to increase clinical homogeneity. Since ethnic heterogeneity and relatedness may affect the distribution of genetic variation and consequently gene expression, de Jong et al. removed non-Caucasian subjects by principal component analysis of SNP array data.

Analysis of Expression Data

The raw microarray data is MIAME compliant and made available at gene expression omnibus (GEO) under accession GSE38485. First, the raw data was (pantile-normalized to correct for overall signal intensity differences among the Illumina human gene expression arrays. Potential batch effects due to date of generation of batch, and because of the use of two different platforms (Illumina HumanRef-8 V3 arrays for batch 1 and HumanRef-12 V3 arrays) were removed by batch analysis in Partek Genomics Suite. After removal of batch effects, the list of probesets that was determined for a signature to be used for identification of chronic cases of schizophrenia from bipolar disorder and controls was extracted.

Reanalysis of Illumina Dataset

In the independent analysis, an accurate prediction of cases from controls of 70%-80% ROC AUC in the deJong et al dataset was independently arrived at using 20 probesets from the signature analysis. This result is important, as deJong et al., 2012 (de Jong et al., PLoS One 2012; 7(6):

e39498) included two platforms different from the original exon array analysis that were used, a refined homogenous ethnic background, and a different whole blood RNA extraction methodology. This study was able to definitively ascertain which cases were free of antipsychotics, this first analysis contains both medicated (n=92) and non-medicated cases (n=29); thus most medicated and non-medicated cases were classified correctly, indicating that the signature is not reliant on a 'treatment' artifact. Two extra probe sets that mapped to the same transcripts as the exon array were included in the analysis. Note that there are 2 probes for genes HPR, TRIM4. Both probes are included in the diagnostic analysis. No probe sets were found for gene CCDC109B.

TABLE 35

The gene expression for the following 20 probe sets for genes identified in the phase I Affymetrix Whole Blood Exon Array dataset as diagnostic for SZ vs BD vs C. The following transcripts were used from GEO dataset GSE38485.

| Column # | Probeset ID | Gene | Transcript | p (SZ vs C) |
|---|---|---|---|---|
| 21001 | ILMN_1766551 | CPA3 | ILMN_19388 ILMN_19388 | 0.0220352 |
| 9052 | ILMN_1694432 | CRIP2 | ILMN_29728 ILMN_29728 | 0.020197 |
| 27078 | ILMN_1805344 | DDX5 | ILMN_20253 ILMN_20253 | 0.041188 |
| 16539 | ILMN_1738383 | EEF2 | ILMN_137242 ILMN_163595 | 0.00422672 |
| 42174 | ILMN_2075065 | FADS2 | ILMN_18999 ILMN_18999 | 0.337777 |
| 9711 | ILMN_1697916 | GYLTL1B | ILMN_23778 ILMN_23778 | 0.0598434 |
| 12343 | ILMN_1712751 | HADHA | ILMN_19990 ILMN_172930 | 0.319209 |
| 9628 | ILMN_1697499 | HLA-DRB5 | ILMN_3178 ILMN_3178 | 0.23479 |
| 27713 | ILMN_1809212 | HPR | ILMN_169425 | 0.48257 |
| 43600 | ILMN_2155452 | HPR | ILMN_169425 ILMN_169425 | 0.693287 |
| 19423 | ILMN_1756455 | IL5RA | ILMN_1894 ILMN_17920 | 0.6403 |
| 46474 | ILMN_2327812 | IL5RA | ILMN_1894 ILMN_1894 | 0.572508 |
| 27014 | ILMN_1804929 | OXTR | ILMN_7313 ILMN_7313 | 0.299299 |
| 3026 | ILMN_1664464 | PTGDS | ILMN_19248 ILMN_19248 | 6.55E−06 |
| 17495 | ILMN_1744003 | SLC44A5 | ILMN_13591 ILMN_13591 | 0.971099 |
| 14712 | ILMN_1726928 | TCEA3 | ILMN_27218 ILMN_27218 | 0.0850903 |
| 44519 | ILMN_2205322 | TREML4 | ILMN_24817 ILMN_24817 | 0.542362 |
| 25033 | ILMN_1792265 | TRIM4 | ILMN_5721 ILMN_8530 | 0.0626756 |
| 46384 | ILMN_2323385 | TRIM4 | ILMN_8530 ILMN_8530 | 0.938466 |
| 47890 | ILMN_2386179 | ZMYND8 | ILMN_26803 ILMN_26803 | 0.00222525 |

First, reproducibility of the 5 gene diagnostic (TCEA3, GYLTL1B, SLC44A5, IL5RA, DDX5) using the two probe sets for IL5RA was analyzed. The overall ROC was marginally diagnostic with AUC=0.637. However, there appeared to be good reproducibility of the diagnostic signature in males under 30 yrs of age. In the young male subgroup, the two IL5RA probe sets and the DDX5 probe set were statistically significant contributors in the logistic model. In Table 36, are results for all subjects broken down by age and gender from the independent deJong et al., 2012 study (de Jong et al., PLoS One 2012; 7(6): e39498).

TABLE 36

ROC characteristics of de Jong et al., 2012 study using 5 genes diagnostic (TCEA3, GYLTL1B, SLC44A5, IL5RA, DDX5) to diagnose SZ compared to control (C).

| Gender | Age | # SZ | # C | ROC AUC | Sensitivity | Specificity |
|---|---|---|---|---|---|---|
| Male | <30 | 21 | 25 | 0.802 | 85.71 | 64.00 |
| Female | <30 | 10 | 19 | 0.684 | 70.00 | 68.42 |
| Male | ≥30 | 66 | 33 | 0.684 | 45.45 | 90.91 |
| Female | ≥30 | 24 | 41 | 0.697 | 45.83 | 90.24 |

Next, the reproducibility of the 11 genes BD+SZ vs NC diagnostic (HPR, TREML4, ZMYND8, PTGDS, CPA3, TRIM4, SLC44A5, HADHA, CCDC109B, EEF2) was analyzed using the two probe sets for TRIM4. Only one of the probe sets for HPR, had gene expression data for all subjects so this was the one included. Again, there was no Illumina expression for CCDC109B to include. The overall ROC was marginally diagnostic with AUC=0.693. However, there appears to be good reproducibility of the diagnostic in all subgroups when stratified by age and gender. In the young (<30) subgroup, the TREML4, PTGDS and one of the TRIM4 probe sets were statistically significant contributors in the logistic model. In Table 37 are the results for all subjects broken down by age and gender.

TABLE 37

ROC characteristics of de Jong et al., 2012 study using gene probesets to test the reproducibility of the 11 genes BD + SZ vs NC diagnostic (HPR, TREML4, ZMYND8, PTGDS, CPA3, TRIM4, SLC44A5, OXTR, HADHA, CCDC109B, EEF2).

| Gender | Age | # SZ | # C | ROC AUC | Sensitivity | Specificity |
|---|---|---|---|---|---|---|
| Male | <30 | 21 | 25 | 0.857 | 76.19 | 84.00 |
| Female | <30 | 10 | 19 | 0.916 | 100.0 | 78.95 |
| Male | ≥30 | 66 | 33 | 0.748 | 74.24 | 78.79 |
| Female | ≥30 | 24 | 41 | 0.806 | 79.17 | 80.49 |

Finally the antipsychotic-free patients and controls were considered using lumina SZ genes, logistic regression fit to data, subgrouped by age <30 and/or neuroleptic-free status (Table 38).

TABLE 38

The ROC to diagnose antipsychotic-free patients and control subjects from de Jong et al., 2012 (de Jong et al., PLoS One 2012; 7(6): e39498) gene expression were TREML4, PTGDS, SLC44A5, GYLTL1B, HPR, TRIM4, CPA3

| Subjects | NC N | SZ N | ROC AUC | Sensitivity | Specificity |
|---|---|---|---|---|---|
| Neuroleptic-free Illumina Subjects | 22 | 15 | 0.642 | 80.0% | 59.1% |
| Neuroleptic-free, Age <30 Subjects | 14 | 8 | 0.866 | 100.0% | 71.4% |

Example 9: SZ-NC Comparison

These results demonstrate the identification of a gene panel to discriminate bipolar schizophrenics from normal controls from 122 top known genes. Forward stepwise variable selection with logistic regression modeling was used to identify a set of genes which would significantly differentiate the bipolar subjects from the normal controls.

Table 39 provides a listing of the set of 5 genes diagnostic for this purpose:

TABLE 39

| Marker | Transcript ID | Gene |
|---|---|---|
| 28 | 2401347 | TCEA3 |
| 53 | 3329099 | GYLTL1B |
| 41 | 2418570 | SLC44A5 |
| 72 | 2660617 | IL5RA |
| 106 | 3766893 | DDX5 |

Table 40 provides the model it for visits 2 and 4.

TABLE 40

Visits 2 and 4
AIC Intercept only 168.355
AIC with genes 67.385

| | Estimate | P-value |
|---|---|---|
| intercept $\beta_0$ | −40.2220 | <0.0001 |
| marker 28 coefficient $\beta_1$ | 6.4838 | <0.0001 |
| marker 53 coefficient $\beta_2$ | −4.7465 | <0.0001 |
| marker 41 coefficient $\beta_3$ | 2.3179 | <0.0001 |
| marker 72 coefficient $\beta_4$ | 2.8666 | <0.0001 |
| marker 106 coefficient $\beta_5$ | −2.5694 | 0.0005 |
| ROC AUC | 0.967 | <0.0001 |

$$\text{Prob of Normal from Logistic} = \frac{1}{1 + \exp[-(\beta_0 + \beta_1 M28 + \beta_2 M53 + \beta_3 M41 + \beta_4 M72 + \beta_5 M106)]}$$

The diagnostic measure for discriminating two populations is that a patient is diagnosed as having Schiz if the Prob(NC) from Logistic 0.3323 (optimal cut-point).

At this cut-point, across both visits, Sensitivity=86.67 (95% CI 75.4–94.1) and Specificity=93.33 (95% CI 83.8–98.2)

Figure 11:
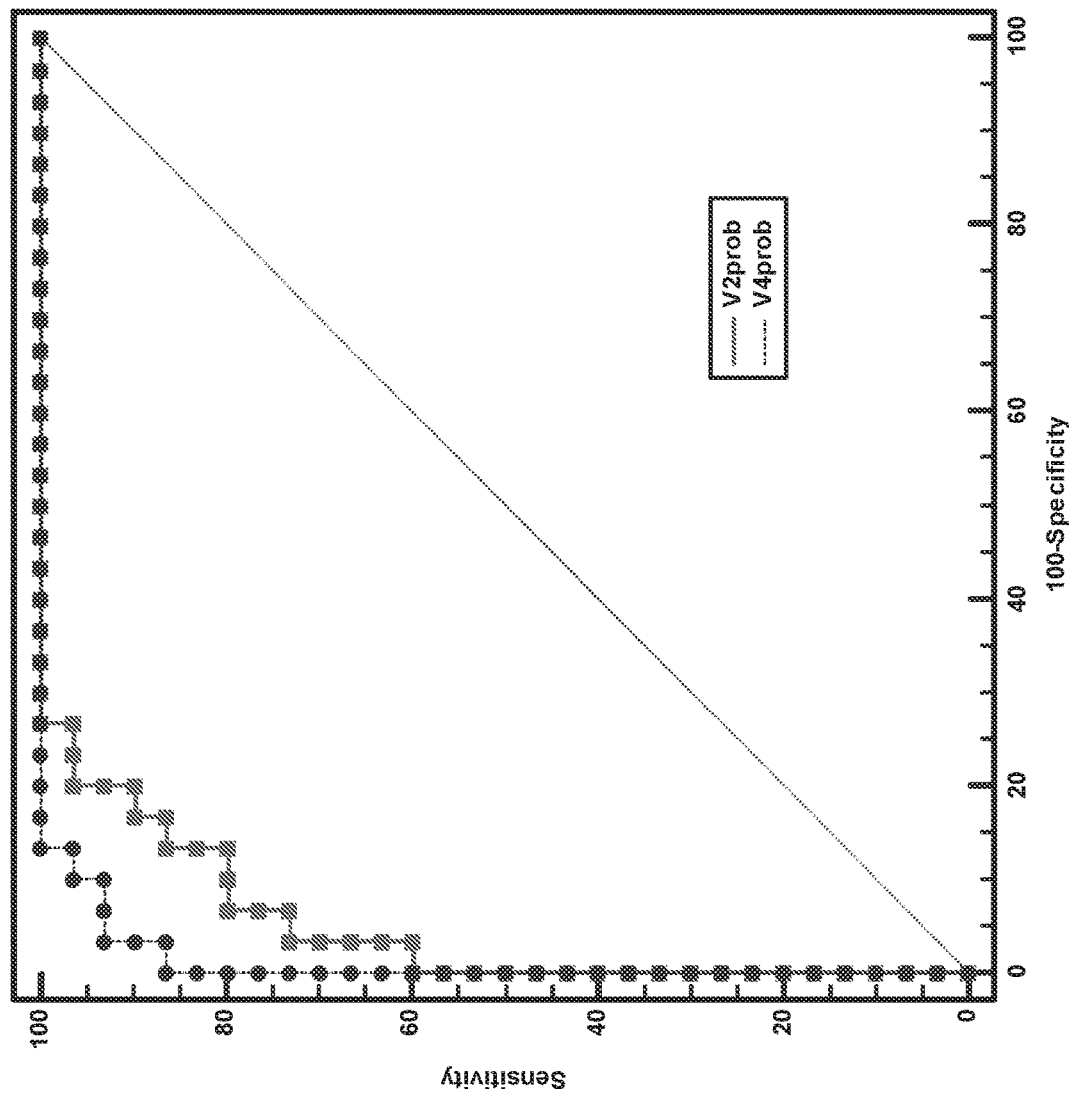
FIG. 11 is a graph of experimental data demonstrating the ROC curve for visits 2 and 4 for SZ vs NC.

FIG. 11 depicts the ROC Curve for visits 2 and 4.

Table 41 depicts the diagnostic of patients using the 0.3323 cut-point for a positive test.

TABLE 41

| | Visit 2 | | Visit 4 | |
|---|---|---|---|---|
| Gene Model | NC | SZ | NC | SZ |
| ≤0.3323 | 3 | 24 | 1 | 28 |
| >0.3323 | 27 | 6 | 29 | 2 |

Visit Specific Metrics:

| | | |
|---|---|---|
| Sensitivity | 0.800 | 0.933 |
| Specificity | 0.900 | 0.967 |
| Accuracy | 0.850 | 0.964 |

Figure 12:
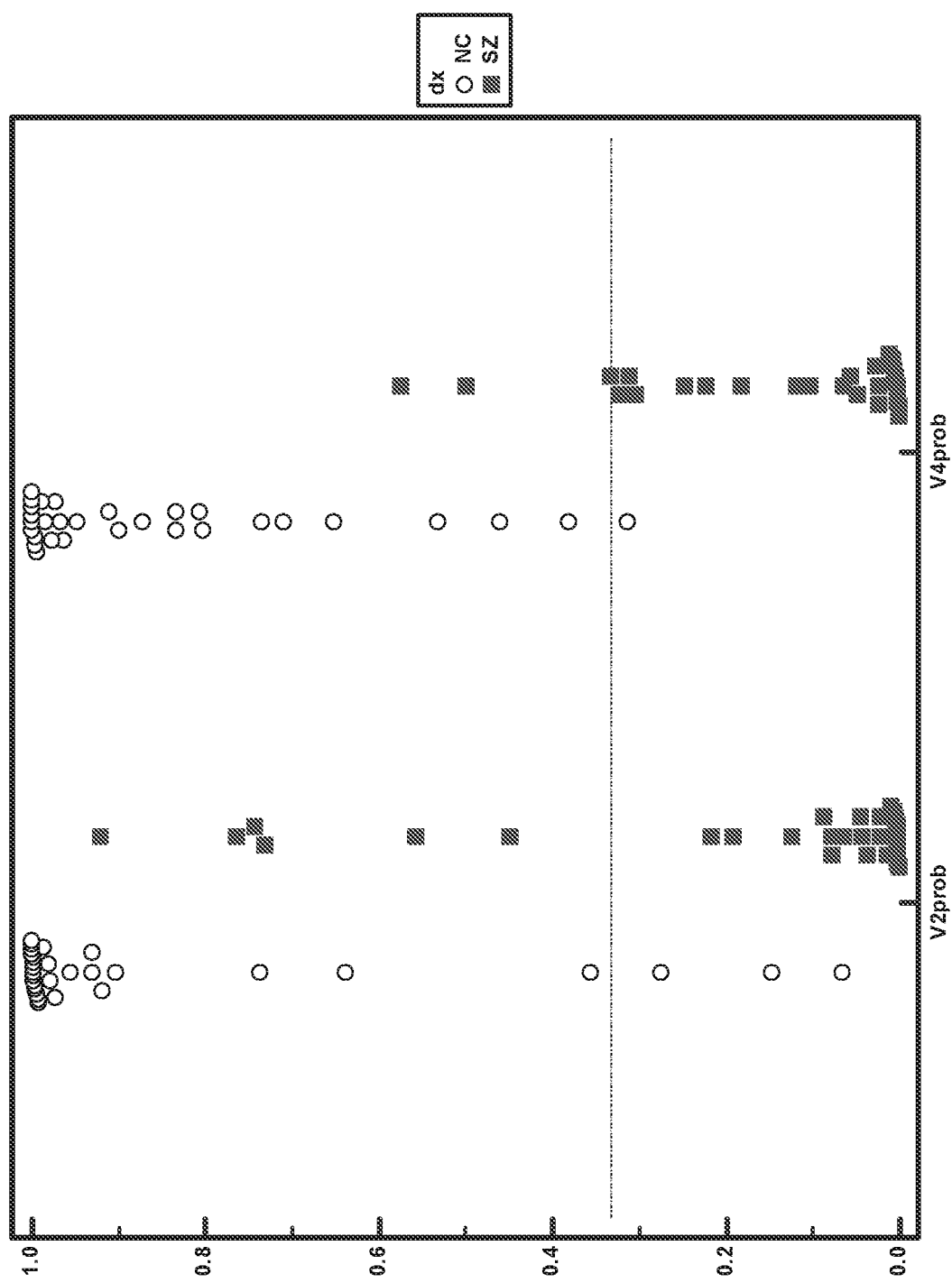
FIG. 12 is a graph of experimental data demonstrating the logistic model estimated probabilities for each group.

FIG. 12 shows the logistic model estimated probabilities for each group, for each visit along with the reference line for the 0.3323 cut-point. The visit 2 probabilities are significantly correlated with the visit 4 probabilities (p<0,0001) with r=0.74 (95% CI 0.59–0.83).

Table 42 demonstrates that 83% of the subjects (50/60) received the same diagnostic outcome from visit 2 to visit 4.

TABLE 42

| | Visit 4 | |
|---|---|---|
| Visit 2 | ≤0.3323 | >0.3323 |
| ≤0.3323 | 27 | 6 |
| >0.3323 | 4 | 23 |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A method of reducing the manifestation and/or progression of bipolar disorder (BD) and schizophrenia (SZ) in a human subject having BD or SZ comprising administering to the human subject one or more clinically approved antipsychotic drugs, wherein the human subject has been selected for administration of the one or more clinically approved antipsychotic drugs after completion of a 4-part gene expression assay on a sample of blood or cells from the human subject, wherein the human subject has been classified as having BD or SZ prior to the administration of the one or more antipsychotic drugs after (a) measuring the mRNA expression levels of each gene in the group consisting of SLC44A5, HADHA, CPA3, OXTR, CCDC109B, TREML4, TRIM4, PTGDS, HPR, EEF2, ZMYND8, TCEA3, IL5RA, GYLTL1B, FADS2, CRIP2, DDX5, and HLA-DRB5 in the sample and (b) correlating those measured levels with either BD or SZ by a logistic regression method comprising the following steps:

(i) first, the measured mRNA levels of each of the genes SLC44A5, HADHA, CPA3, OXTR, CCDC109B, TREML4, TRIM4, PTGDS, HPR, EEF2, and ZMYND8 are each multiplied by an associated weight factor and then added to form a weighted sum value; and the weighted sum value compared against a reference threshold, wherein a weighted sum value equal to or below this reference threshold identifies the subject as suspected of developing or having BD or SZ; then, second, (ii) if the human subject is suspected of developing or having BD or SZ after step (i), the weighted sum value of the measured mRNA expression levels of each of the genes OXTR, PTGDS, FADS2, and HLA-DRB5 in the sample is calculated and compared against a reference threshold, wherein a weighted sum value equal to or below this reference threshold identifies the human subject as suspected of developing or having BD; and then, third, (iii) if the human subject is suspected of developing or having BD or SZ after step (i), the weighted sum value of the measured mRNA expression levels of the genes TCEA3, SLC44A5, IL5RA, GYLTL1B, and DDX5 in the sample is calculated and compared against a reference threshold, wherein a weighted sum value equal to or below this reference threshold identifies the human subject as suspected of developing or having SZ; and then, fourth, (iv(a)) if the human subject has been identified as suspected of developing or having BD after steps (i)

and (ii), the weighted sum value of the measured mRNA expression levels of the genes OXTR, FADS2, and CRIP2 in the sample is calculated and compared against a reference threshold, wherein a weighted sum value above this reference threshold differentiates and classifies the human subject as having BD and not SZ; and (iv(b)) if the human subject has been identified as suspected of developing or having SZ after steps (i) and (iii), the weighted sum value of the measured mRNA expression levels of the genes OXTR, FADS2, and CRIP2 in the sample is calculated and compared against a reference threshold, wherein a weighted sum value equal to or below this reference threshold differentiates and classifies the human subject as having SZ and not BD;

wherein the multiplication of mRNA levels by associated weight factors, the weighted sum values, and the reference thresholds are parts of the logistic regression method.

2. The method of claim 1, wherein the human subject is less than 30 years of age, prior to the gene expression measurements.

3. The method of any one of claims 1 and 2, wherein the human subject is displaying psychotic feature(s), prior to the gene expression measurements.

4. The method of any one of claims 1 and 2, wherein the subject is displaying BD and/or SZ features selected from those identified based on the Diagnostic and Statistical Manual of Mental Illnesses (DSM) criteria, prior to the gene expression measurements.

5. The method of any one of claims 1 and 2, wherein the subject is at high clinical risk, in a prodromal phase, and not yet diagnosed with schizophrenia, prior to the gene expression measurements.

6. The method of any one of claims 1 and 2, wherein the subject is at high clinical risk, in a prodromal phase, and not yet diagnosed with bipolar disorder, prior to the gene expression measurements.

7. The method of any one of claims 1 and 2, wherein the mRNA expression level of each gene is measured by hybridization of a gene array consisting of probes for said genes, RT-PCR, northern blot, nuclease protection, real time PCR, branched DNA, nucleic acid sequence-based amplification (NASBA), RNA Sequencing, digital droplet PCR, and/or differential display.

8. The method of any one of claims 1 and 2, wherein the cells are isolated from the blood.

9. The method of any one of claims 1 and 2, wherein the sample is a blood sample.

10. The method of claim 8, wherein the mRNA expression level of each gene is measured by hybridization of a gene array consisting of probes for said genes, RT-PCR, northern blot, nuclease protection, real time PCR, branched DNA, nucleic acid sequence-based amplification (NASBA), RNA Sequencing, digital droplet PCR, and/or differential display.

11. The method of claim 9, wherein the mRNA expression level of each gene is measured by hybridization of a gene array consisting of probes for said genes, RT-PCR, northern blot, nuclease protection, real time PCR, branched DNA, nucleic acid sequence-based amplification (NASBA), RNA Sequencing, digital droplet PCR, and/or differential display.

12. The method of claim 5, wherein the mRNA expression level of each gene is measured by hybridization of a gene array consisting of probes for said genes, RT-PCR, northern blot, nuclease protection, real time PCR, branched DNA, nucleic acid sequence-based amplification (NASBA), RNA Sequencing, digital droplet PCR, and/or differential display.

13. The method of claim 6, wherein the mRNA expression level of each gene is measured by hybridization of a gene array consisting of probes for said genes, RT-PCR, northern blot, nuclease protection, real time PCR, branched DNA, nucleic acid sequence-based amplification (NASBA), RNA Sequencing, digital droplet PCR, and/or differential display.

14. The method of claim 1, wherein the subject is antipsychotic drug-free, prior to the gene expression measurements.

* * * * *